(12) United States Patent
Hjarn et al.

(10) Patent No.: US 10,542,943 B2
(45) Date of Patent: Jan. 28, 2020

(54) SCANNING MAMMOGRAPHY X-RAY SYSTEM WITH MOVEMENT ADAPTION MECHANISM

(71) Applicant: KONINKLIJKE PHILIPS N.V., Eindhoven (NL)

(72) Inventors: Torbjorn Hjarn, Vaxholm (SE); Bo Frånberg, Spånga (SE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 245 days.

(21) Appl. No.: 15/540,037

(22) PCT Filed: Jan. 4, 2016

(86) PCT No.: PCT/EP2016/050038
§ 371 (c)(1),
(2) Date: Jun. 27, 2017

(87) PCT Pub. No.: WO2016/110470
PCT Pub. Date: Jul. 14, 2016

(65) Prior Publication Data
US 2017/0347972 A1    Dec. 7, 2017

(30) Foreign Application Priority Data

Jan. 6, 2015    (EP) .................................... 15150132

(51) Int. Cl.
*A61B 6/02*    (2006.01)
*A61B 6/00*    (2006.01)

(52) U.S. Cl.
CPC .............. *A61B 6/025* (2013.01); *A61B 6/027* (2013.01); *A61B 6/502* (2013.01); *A61B 6/40* (2013.01)

(58) Field of Classification Search
CPC ......... A61B 6/025; A61B 6/027; A61B 6/502; A61B 6/40
See application file for complete search history.

(56) References Cited

U.S. PATENT DOCUMENTS 5,388,141 A * 2/1995 Hove ..................... A61B 6/447
378/196
6,574,499 B1 * 6/2003 Dines ................... A61B 6/0414
128/915

(Continued)

FOREIGN PATENT DOCUMENTS

| EP | 1428473 | 6/2004 |
|---|---|---|
| WO | 2014/011681 | 1/2014 |
| WO | 2014/151856 | 9/2014 |

*Primary Examiner* — David P Porta
*Assistant Examiner* — Djura Malevic
(74) *Attorney, Agent, or Firm* — Larry Liberchuk

(57) ABSTRACT

The present invention relates to mammography, e.g. tomosynthesis mammography. In order to provide a mammography X-ray imaging with improved data quality, a mammography X-ray imaging system (10) for tomosynthesis mammography is provided that comprises an X-ray source (12), an X-ray detector (14), a support structure (22), and a breast support (18) with a breast support surface (20). The X-ray source and the X-ray detector are mounted on an upwardly extending scan arm (24); the X-ray source is mounted on the scan arm above the breast support and the X-ray detector is mounted below the breast support. The scan arm is movably mounted to the support structure to perform a swivelling motion about a rotation axis (26) located below the breast support. During the swivelling motion, the scan arm swivels about the rotation axis such that the X-ray source and the X-ray detector perform a scan motion and an object on the breast support is radiated from different angular directions. A motion adapting mechanism (34) is provided that, during the scan motion, moves the (Continued)

X-ray detector along an adapted trajectory (36) that follows the breast support surface. In an example, the adapted trajectory is in alignment with the breast support surface.

14 Claims, 15 Drawing Sheets

(56) References Cited

U.S. PATENT DOCUMENTS

| | | | | |
|---|---|---|---|---|
| 6,979,123 | B2* | 12/2005 | Barta | A61B 6/447 378/197 |
| 7,123,683 | B2* | 10/2006 | Tsujii | A61B 6/0457 378/26 |
| 7,302,031 | B2* | 11/2007 | Hjarn | A61B 6/02 378/23 |
| 7,453,979 | B2* | 11/2008 | Sendai | A61B 6/025 378/23 |
| 8,246,249 | B2 | 8/2012 | Sokolov | |
| 8,452,379 | B2 | 5/2013 | DeFreitas | |
| 9,451,923 | B2* | 9/2016 | Hemmendorff | A61B 6/4452 |
| 9,510,798 | B2* | 12/2016 | Mao | A61B 6/4441 |
| 9,693,741 | B2* | 7/2017 | Kobayashi | A61B 6/502 |
| 9,848,838 | B2* | 12/2017 | Souchay | A61B 6/025 |
| 10,130,322 | B2* | 11/2018 | Moon | A61B 6/0421 |
| 2004/0028176 | A1* | 2/2004 | Kamenetsky | A61B 6/0414 378/37 |
| 2004/0208289 | A1* | 10/2004 | Barta | A61B 6/447 378/197 |
| 2005/0234327 | A1* | 10/2005 | Saracen | A61B 6/0457 600/407 |
| 2008/0101537 | A1* | 5/2008 | Sendai | A61B 6/025 378/23 |
| 2010/0007659 | A1 | 1/2010 | Ludwig | |
| 2010/0091940 | A1* | 4/2010 | Ludwig | A61B 6/025 378/22 |
| 2010/0260316 | A1* | 10/2010 | Stein | A61B 6/025 378/37 |
| 2010/0316186 | A1* | 12/2010 | Hyvarinen | A61B 6/0414 378/37 |
| 2012/0045111 | A1* | 2/2012 | Palma | G06T 7/0012 382/132 |
| 2012/0170712 | A1* | 7/2012 | Popova | A61B 6/025 378/37 |
| 2012/0219121 | A1* | 8/2012 | Simmons | A61B 6/4405 378/198 |
| 2012/0224673 | A1* | 9/2012 | Barker | A61B 6/4405 378/198 |
| 2012/0328074 | A1* | 12/2012 | Souchay | A61B 6/025 378/37 |
| 2013/0300737 | A1* | 11/2013 | Nishino | A61B 6/022 345/419 |
| 2014/0072100 | A1 | 3/2014 | Jang | |
| 2014/0133626 | A1* | 5/2014 | Jang | A61B 6/542 378/62 |
| 2014/0140472 | A1* | 5/2014 | Hemmendorff | A61B 6/025 378/19 |
| 2014/0185746 | A1* | 7/2014 | Baturin | A61B 6/484 378/36 |
| 2014/0198896 | A1* | 7/2014 | Hemmendorff | A61B 6/4452 378/37 |
| 2014/0348291 | A1* | 11/2014 | Lee | A61B 6/502 378/37 |
| 2015/0157282 | A1* | 6/2015 | Kobayashi | A61B 6/502 378/37 |
| 2016/0000386 | A1* | 1/2016 | Souchay | A61B 6/025 378/37 |
| 2016/0089093 | A1* | 3/2016 | Mao | A61B 6/4441 378/198 |
| 2016/0100760 | A1* | 4/2016 | Ryu | A61B 6/5247 600/414 |
| 2016/0166222 | A1* | 6/2016 | Kim | A61B 6/502 378/37 |
| 2016/0317112 | A1* | 11/2016 | Roessl | A61B 6/4291 |

* cited by examiner

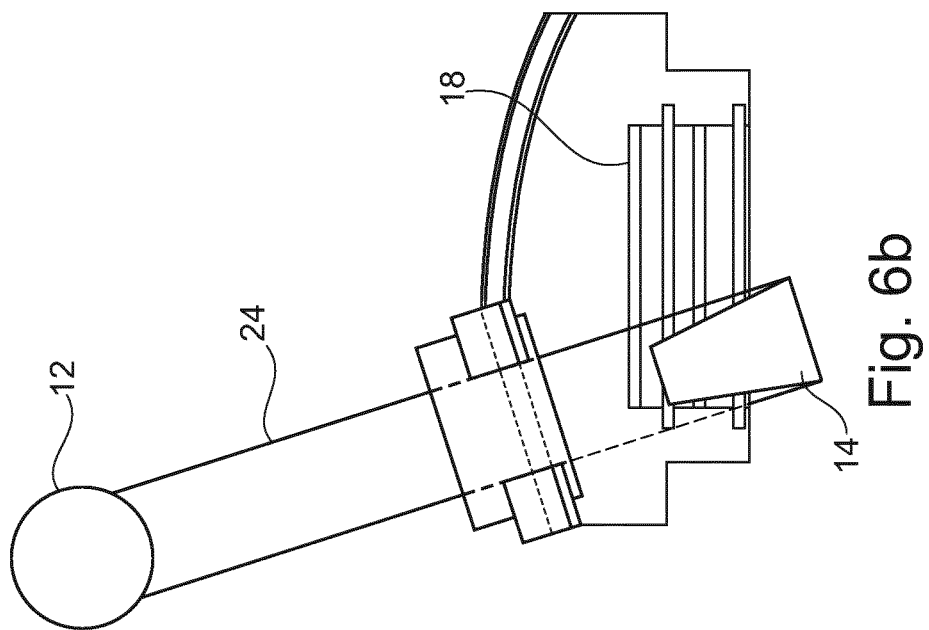
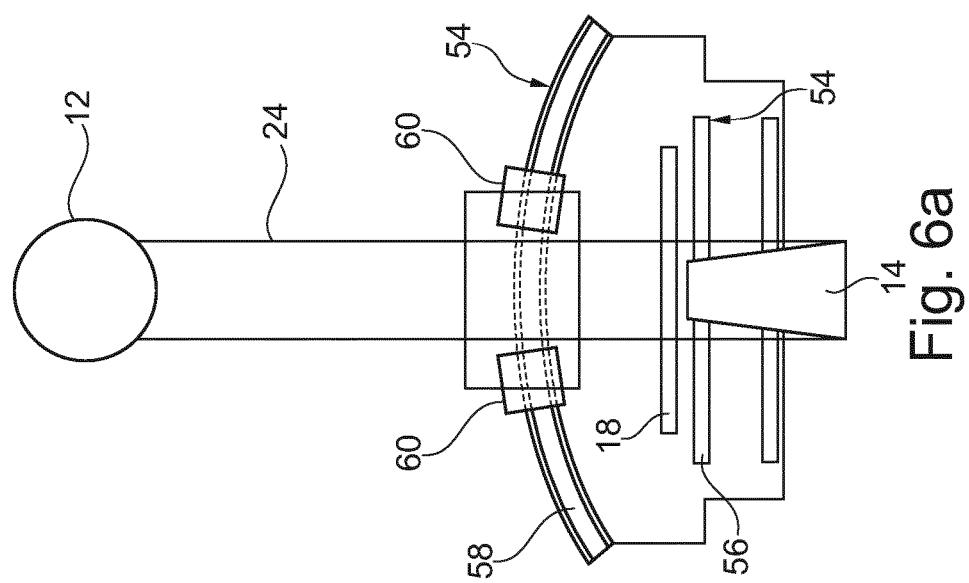

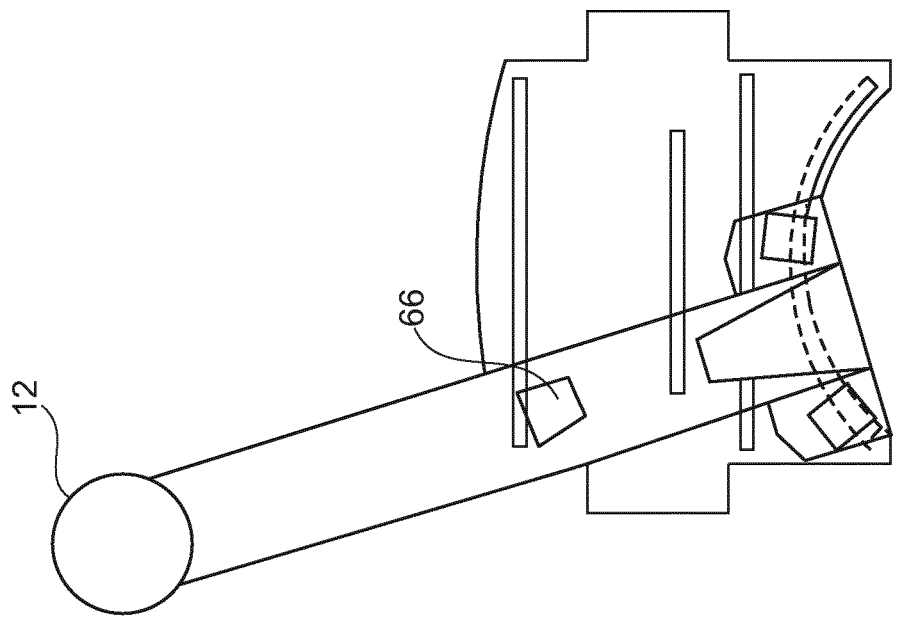
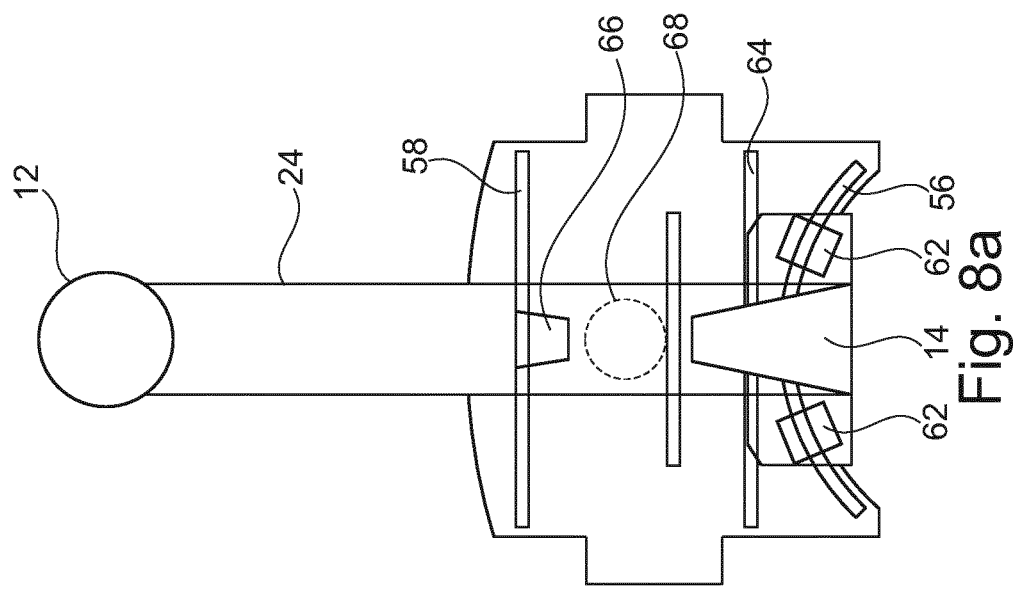

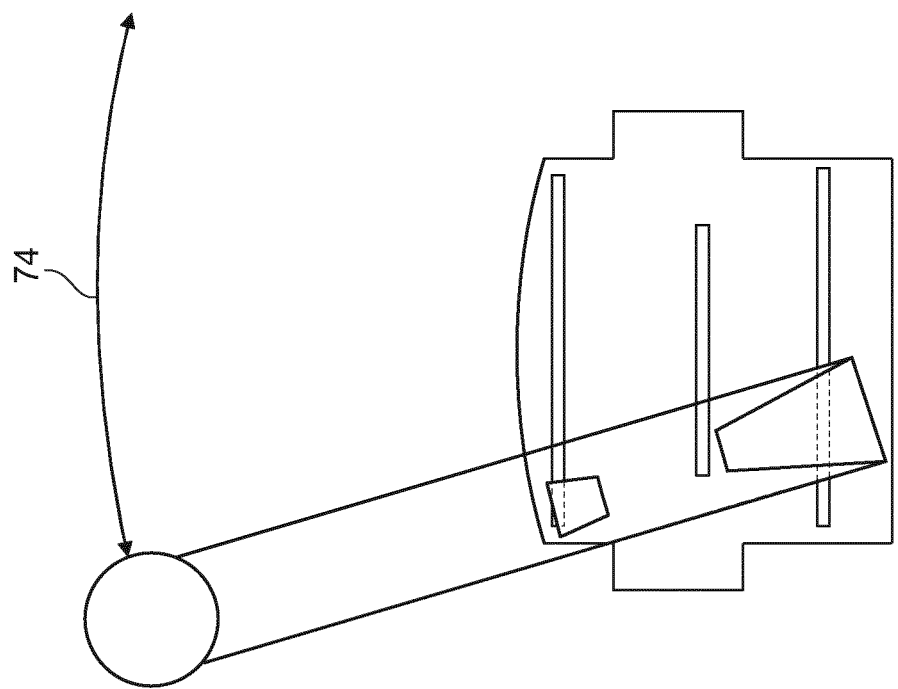
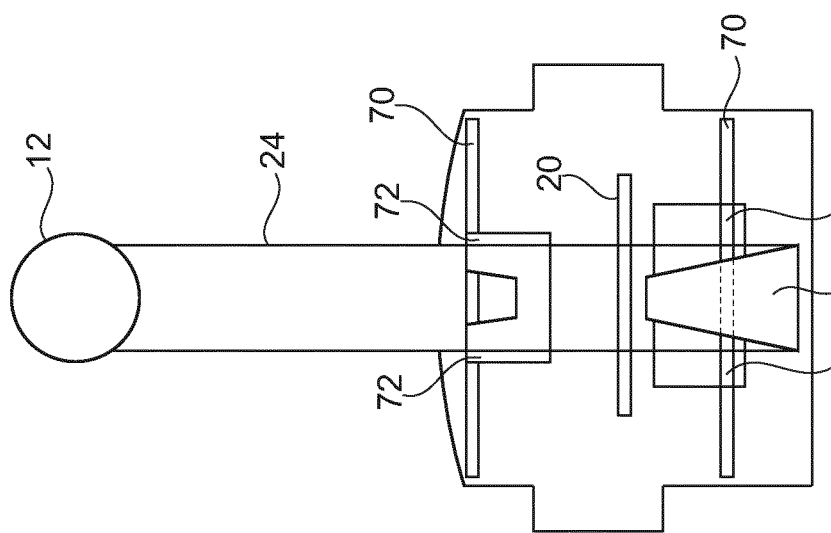

US 10,542,943 B2

SCANNING MAMMOGRAPHY X-RAY SYSTEM WITH MOVEMENT ADAPTION MECHANISM

CROSS REFERENCE TO RELATED APPLICATIONS

This application is the U.S. National Phase application under 35 U.S.C. § 371 of International Application No. PCT/EP2016/050038 filed Jan. 4, 2016, published as WO 2016/110470 on Jul. 14, 2016, which claims the benefit of European Patent Application Number 15150132.7 filed Jan. 6, 2015. These applications are hereby incorporated by reference herein.

FIELD OF THE INVENTION

The present invention relates to mammography, and relates in particular to a mammography X-ray imaging system for tomosynthesis mammography and a method for providing mammography X-ray image data for tomosynthesis mammography.

BACKGROUND OF THE INVENTION

For breast examination purposes, X-ray imaging is used. For example, to reconstruct a three-dimensional image of a patient's breast, tomosynthesis is used. For tomosynthesis mammography, a number of images are acquired, wherein the focal spot of the X-ray source is rotating in relation to the object, i.e. the breast. The data comprising a number of 2D projection images is used for reconstructing a 3D image. U.S. Pat. No. 7,302,031 B2 describes X-ray imaging for three-dimensional imaging, in particular for tomosynthesis examination, such as for tomosynthesis mammography. US 2014/0198896 A1 also relates to tomosynthesis mammography and describes adapting a scan motion in an X-ray imaging apparatus. However, it has been shown that the requirements for the acquired image data are constantly increasing and that improved quality of the acquired image data would be desirable in order to provide improved reconstructed 3D image data.

EP1428473A2 describes an X-ray tomosynthesis system for forming a three-dimensional image of an object including an X-ray detector which is adapted to move relative to the object.

SUMMARY OF THE INVENTION

There may thus be a need to provide mammography X-ray imaging acquiring image data with better data quality.

The object of the present invention is solved by the subject-matter of the independent claims, wherein further embodiments are incorporated in the dependent claims. It should be noted that the following described aspects of the invention apply also for the mammography X-ray imaging system and the method for providing mammography X-ray image data.

According to a first aspect of the present invention, a mammography X-ray imaging system for tomosynthesis mammography is provided that comprises an X-ray source, an X-ray detector, a support structure and a breast support with a breast support surface. The X-ray source and the X-ray detector are mounted on an upwardly extending scan arm. The X-ray source is mounted on the scan arm above the breast support and the X-ray detector is mounted on the scan arm below the breast support. The scan arm is movably mounted to the support structure to perform a swivelling motion about (or: around) a rotation axis located below the breast support and at a position substantially below the X-ray detector when the scan arm is in vertical position. During the swivelling motion, the scan arm swivels about the rotation axis such that the X-ray source and the X-ray detector perform a scan motion, and an object on the breast support is radiated from different angular directions. A motion adapting mechanism is provided that, during the scan motion, moves the X-ray detector along an adapted trajectory that follows the breast support surface.

According to an example, the adapted trajectory is in alignment with the breast support surface.

As an effect, an improved image quality is achieved, since the distance between the detector and the object is maintained throughout the scan motion, i.e. the distance is kept to a minimum. By acquiring image data with more or less the same distance between object and detector, the image data of the different slices can be combined in a facilitated manner and thus leads to a better image result.

According to an example, to move the X-ray detector along the adapted trajectory that follows the breast support, the motion adapting mechanism provides a radial displacement of the X-ray detector in relation to the rotation axis during the scan motion.

The radial displacement provides the effect that during the swivelling motion, the detector can nevertheless move along a more or less straight or linear trajectory, thus following, for example, a linear or straight breast support surface.

According to an example, the X-ray source and the X-ray detector are provided in a fixed relative distance to each other during operation. The motion adapting mechanism moves the X-ray source along an adapted source-trajectory that is adapted in the direction of the breast support surface.

By providing a fixed relative distance between X-ray source and X-ray detector, a fixed geometric relationship is provided, thus facilitating the reconstruction steps.

According to an example, the X-ray source and the X-ray detector are fixedly mounted on the scan arm. In a first example, the rotation axis remains fixed during a scan, and the motion adapting mechanism displaces the scan arm in relation to the rotation axis in radial direction. In a second example, the motion adapting mechanism provides a vertical displacement of the rotation axis, and the scan arm remains fixed in relation to the rotation axis in radial direction.

According an example, a pre-collimator is provided that is mounted to the scan arm. During operation, the motion adapting mechanism moves the pre-collimator along an adapted collimator-trajectory that follows the breast support surface. In an example, the pre-collimator is fixed in relation to source and detector as a set, and the set is moving together.

As an effect, it is possible to radiate breasts with a large variety in size. In particular, the use of a collimator as above, allows the radiation of larger breasts.

According to an example, the motion adapting mechanism comprises at least one guiderail with an extension direction adapted to the breast support surface. The at least one guiderail provides that the X-ray detector follows the breast support surface during the scan motion.

According to an example, the motion adapting mechanism comprises two guiderails. One of the guiderails is provided above the breast support as an upper guiderail, and another one of the guiderails is provided below this upper guiderail as a lower guiderail. At least one of the guiderails provides the swivelling motion of the scan arm about a virtual rotation axis, and at least another one of the guiderails provides that the X-ray detector follows the breast support surface.

In another example, one of the guiderails is provided close above or below the breast support as the upper guiderail, and the other one of the guiderails is provided below this upper guiderail as the lower guiderail.

The term "close above" relates to an arrangement in the proximity of the breast support, e.g. maximum approximately 15 cm, e.g. approximately 10 cm or approximately 5 cm, above the breast support surface.

This provides the effect that a space below the breast support may be occupied only to a minimum extent. The design with virtual rotation axis is creating space useable for legs or knees, e.g. for a seated patient. The space can also be referred to as a leg space, or knee space.

In another example, a sliding function along the guiderails creates a space for receiving a patient's belly, hence a so-called belly space is provided. The reason is that slide scan motion allows a design with lower front side on the patient support cover. The extra space provided is in particular user-friendly for standing and sitting patients.

According to an example, one of the guiderails is a curved guiderail that provides the swivelling motion of the scan arm about a virtual rotation axis. The other one of the guiderails is an at least less-curved guiderail that provides that the X-ray detector follows the breast support surface.

This provides the effect that the guiderails ensure a proper and reliable guidance, thus improving accuracy of the image procedure.

In an example, a curved guiderail has a radius with its centre point representing the axis, i.e. the point of rotation of the scanning movement. Another guiderail controls at least the height position of the scan arm or the detector. The shape of this other (or second) guiderail can have a radius that is larger than the first mentioned guiderail. This second guiderail can also be straight and can even have a reversed shaped radius. The function of the radius is related to the attachment position in height for this guiderail. Further, i.e. more guiderails can be provided with the purpose to handle momentum from the scan arm to reduce its deflection or displacement.

In an example, the other one of the guiderails is a straight linear guiderail, i.e. a guiderail without any curve.

According to an example, the upper guiderail is the curved guiderail and the lower guiderail is the less-curved guiderail. Two movable bearings for the scan arm are provided to move along the upper, curved guiderail for swivelling the scan arm during the scan motion. The two movable bearings are having a fixed distance to each other in direction of the guiderail. The lower guiderail provides for the carrying of the scan arm and for guidance of the X-ray detector to follow the adapted trajectory.

In an example, the movable bearings are arranged on the guiderail to form (fixedly) distanced sliding bearings for the scan arm, i.e. bearings with at least two points of load transfer, which points are arranged to have a fixed distance between them.

The movable bearings are provided to move along the guiderail. For this purpose, the bearings can be equipped with rolling bearing elements, or also with sliding bearing elements.

In another example, the movable bearings are provided as a continuous ball slider covering a respective section of the guiderail. Inside such a ball slider, multiple points of load transfer, i.e. at least two points are provided.

In still another example, curved guides are used ball sliders.

In a still further example, curved guides are used and the bearings have profiled wheels, e.g. a minimum of three wheels, wherein at least one wheel is arranged on each side of the guide. In another example, four or more wheels are provided.

The movable bearings, e.g. sliding bearings, are arranged with a fixed distance to each other to allow not only vertical load transfer, e.g. of weight, but to also allow the support for the arm cantilevering to either side during the scan motion. In other words, the distanced bearings act as one cantilevering support that allows the transfer or force transmission of a static momentum, i.e. a torque directed to the side caused by the scan arm when not being in the vertical position (in which more or less only vertical load is transmitted).

In an example, also applicable for other versions with a curved rail, the two bearings have a fixed distance to each other. They are following the curved rail to create the rotation motion.

This provides the effect that a simple and reliable mechanism is provided for defining the swivelling motion of the scan arm as a central aspect of the motion in tomosynthesis mammography.

The fixed distance is provided such that the bearings are arranged spaced apart to each other.

According to an example, the upper guiderail is the less-curved guiderail and the lower guiderail is the curved guiderail. Two movable bearings for the scan arm are provided to move along the lower, curved guiderail for swivelling the scan arm during the scan motion. The two movable bearings are having a fixed distance to each other in direction of the guiderail (see above). The upper guiderail provides for the carrying of the scan arm, and for guidance of the X-ray detector to follow the adapted trajectory.

According to an example, a third guiderail is provided. The third guiderail is less-curved than the lower, curved guiderail. The third guiderail provides for the carrying of the scan arm, and for guidance of the X-ray detector to follow the adapted trajectory. Further, the upper guiderail provides for additional support of the scan arm In an example, the two movable bearings for the scan arm are provided to move along the lower, curved guiderail for swivelling the scan arm during the scan motion. The two movable bearings are having a fixed distance to each other in direction of the guiderail.

In one option, a pre-collimator is arranged between the X-ray source and an object, e.g. in combination with a line detector. In another option, no pre-collimator is provided, e.g. in combination with other detector types.

In an example, the third guiderail is provided between the lower guiderail and the breast support surface. In a further example, the third guiderail is provided between the lower guiderail and upper guiderail. In a still further example, the third guiderail is mounted above the upper guiderail or below the lower guiderail.

In a further example, the upper guiderail provides for guiding the pre-collimator.

According to an example, at least two guiderails are provided as linear guiderails. Movable bearings are provided for each guiderail to move along the respective guiderail. The swivel motion of the scan arm is provided by a synchronized movement of at least two movable bearings along two of the at least two guiderails. One of the at least two guiderails provides that the X-ray detector follows the breast support surface.

In one example, two guiderails are provided as linear guiderails, i.e. as the upper and lower guiderail. Movable bearings, e.g. sliding bearings, are provided for each guiderail. The swivel motion of the scan arm is provided by a synchronized movement of the two sliding bearings along the upper and lower guiderail. One of the two guiderails provides that the X-ray detector follows the breast support surface.

The bearings on the two guiderails each provide for sliding along the guiderail as primary function, and also for angular adjustment as secondary function. At least one of the bearings additionally provides also for vertical adjustment as third function. In other words, this at least one bearing also provides for a vertical sliding with respect to the scan arm at least within a certain range caused by the angular movement of the scan arm leading to increasing distance between the two support points along the scan arm when the scan arm swivels to the side.

In another example, a third guiderail is provided for the carrying of the scan arm, and for guidance of the X-ray detector to follow the adapted trajectory. This third guiderail can be mounted between the upper and the lower guiderail, but it can also be mounted above the upper guiderail or below the lower guiderail. In this example, the two first mentioned guiderails are used for controlling the angle position of the scan arm, and the third guiderail is used for the height control.

The bearings on the third guiderail provide for sliding along the guiderail as primary function. This is achieved, for example, by a gliding block or sliding block as a part of the bearing. The sliding itself thus provides a primary degree of freedom of movement.

The bearings on the third guiderail are also configured to allow a change of the angular relation between the scan arm and the third guiderail as secondary function. This is achieved, for example, by a pivoting support or swivel joint as a further part of the bearing. The angular change itself thus provides a secondary degree of freedom of movement. However, the primary degree of freedom of movement is at least indirectly controlled by the activation of the actuators. The secondary degree of freedom of movement is also at least indirectly controlled by the activation of the actuators.

The bearings on the third guiderail provide position fixation in a direction transverse to the guiderails' extension to provide support for the pivoting forces caused by the weight of the X-ray imaging arrangement provided in a cantilevered manner with a distance to the support thus generating momentum forces in the supports.

The bearings on the two other guiderails provide for also sliding along the guiderail as primary function. This is achieved, as well, for example, by a gliding block or sliding block as a part of the bearing. The sliding itself thus provides a primary degree of freedom of movement.

The bearings on the two other guiderails are also configured to allow a change of the angular relation between the scan arm and the two other guiderails as secondary function. This is achieved, as well, for example, by a pivoting support or swivel joint as a further part of the bearing. The angular change itself thus provides a secondary degree of freedom of movement.

The bearings on the two other guiderails are further also configured to allow a change of the vertical relation between the scan arm and the two other guiderails as third function. This is achieved, for example, by a second gliding block or sliding block as a part of the bearing, which second gliding block is arranged between the swivel joint and the scan arm. The further sliding itself thus provides a third degree of freedom of movement. However, again, the primary and secondary degrees of freedom of movement are at least indirectly controlled by the activation of the actuators. Further also the third degree of freedom of movement is also at least indirectly controlled by the activation of the actuators, which control the scan arm's motion.

In other words, the bearings on the two other guiderails also provide for a vertical sliding with respect to the scan arm at least within a certain range caused by the angular movement of the scan arm leading to increasing distance between the two support points along the scan arm when the scan arm swivels to the side.

The bearings on the two other guiderails also provide for fixation in a direction transverse to the guiderails' extension to provide support for the pivoting forces caused by the weight of the X-ray imaging arrangement provided in a cantilevered manner with a distance to the support thus generating momentum forces in the supports.

According to an example, the surface of the breast support is provided as a flat surface for supporting the breast. During the scan motion, the X-ray detector moves along an adapted trajectory, thus following the flat surface.

According to an example, the surface of the breast support is provided as a concave surface for supporting a breast. During the scan motion, the X-ray detector moves along an arc trajectory, thus following the concave surface, which concave arc is having a virtual rotation axis arranged above the breast support.

According to an example, the X-ray detector is a line-detector comprising a plurality of strip detector segments.

According to an example, the X-ray detector is a photon-counting detector.

According to a second aspect of the present invention, a method for providing mammography X-ray image data for tomosynthesis mammography is provided. The method comprises the following steps:

a) An object of interest, e.g. a breast, is arranged on a breast support surface of a breast support.

b) The object is scanned with radiation provided by an X-ray source towards an X-ray detector. The X-ray source and the X-ray detector are mounted on an upwardly extending scan arm. The X-ray source is mounted on the scan arm above the breast support and the X-ray detector is mounted on the scan arm below the breast support. The scan arm is movably mounted to a support structure to perform a swivelling motion about a rotation axis located below the breast support and at a position substantially below the X-ray detector when the scan arm is in vertical position.

During the scanning in step b), the scan arm is swivelling about the rotation axis such that the X-ray source and the X-ray detector perform a scan motion and the object on the breast support is radiated from different angular directions.

During the scanning in step b), a motion adapting mechanism is moving the X-ray detector along an adapted trajectory that follows the breast support surface. During the scanning in step b), X-ray radiation that has passed the object is detected by the detector.

According to the present invention, a swivelling scanning motion of an X-ray source and detector are provided for acquiring 3D data by X-ray radiation from a plurality of directions. In an example, photons are detected that have passed the object in different directions. The respective data is reconstructed into a 3D volume, and this volume can then be presented like slices with a selected thickness and it is also possible to reconstruct synthetic 2D images. However, the movement of the X-ray detector during the swivelling scan motion is modified to such an extent that the X-ray detector moves in a close distance to the breast support surface, which distance is varying only to a minimum extent.

This results in a gain of spatial resolution, for example. Hence, improved image data is achievable. Further, by, for example, replacing a real point of rotation with a virtual point of rotation for the swivelling motion, constructional space below the breast support is no longer occupied and can be used for improving the user friendliness of the imaging system. If the system is equipped with a pre-collimator to reduce radiation and increase image quality, e.g. a pre-collimator with a sliding movement, which movement is also, in one example, provided along an adapted trajectory, the pre-collimator is less space reducing, and is thus providing a larger volume for receiving a breast. In other words, the system is also suitable for larger breasts. As an option, the adapted and flattened trajectory reduces the distance between the pre-collimator and the object in the middle part of the of the scan movement. This shorter distance increases the performance for image quality, e.g. the quality related to modular transfer function.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings:

FIG. 6A and FIG. 6B show a further example of a mammography X-ray imaging system;

FIG. 8A and FIG. 8B show a further example of a mammography X-ray imaging system;

FIG. 9A and FIG. 9B show a still further example of a mammography X-ray imaging system;

DETAILED DESCRIPTION OF EMBODIMENTS

Figure 1:
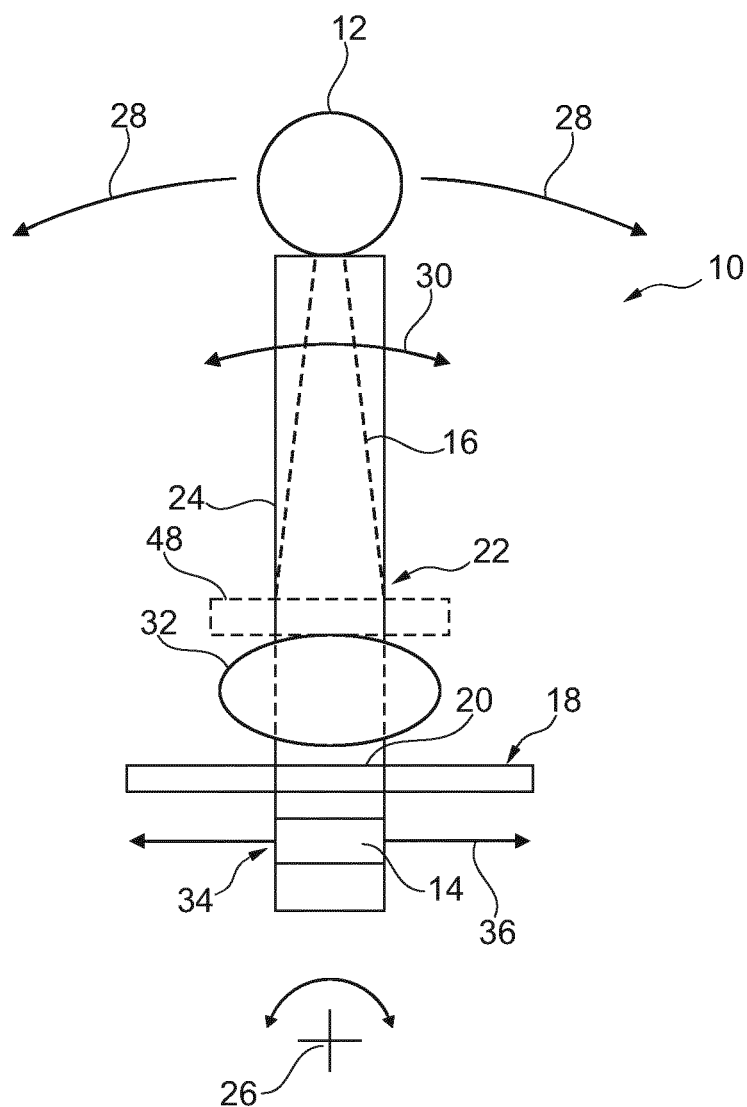
FIG. 1 shows a schematic setup of an example of a mammography X-ray imaging system.

FIG. 1 shows a mammography X-ray imaging system 10 for tomosynthesis mammography. The system comprises an X-ray source 12 and an X-ray detector 14. The X-ray source 12 generates X-ray radiation 16 projecting in a direction towards the detector 14. Further, a breast support 18 with a breast support surface 20 is provided. Still further, also a support structure 22 is provided (shown in FIG. 2). However, for better visibility of the other features, the support structure is not shown in FIG. 1.

The X-ray source 12 and the X-ray detector 14 are mounted on an upwardly extending scan arm 24. The X-ray source 12 is mounted on the scan arm 24 above the breast support 18, and the X-ray detector 14 is mounted on the scan arm 24 below the breast support 18.

The scan arm is movably mounted to the support structure 22 (not further shown in FIG. 1) to perform a swivelling motion about a rotation axis 26 located below the breast support and at a position below the X-ray detector 14 when the scan arm 24 is in vertical position. The swivelling motion is indicated with two arrows 28 and another double arrow 30 indicating the swivelling motion of the scan arm 24. During the swivelling motion, the scan arm 24 swivels about (or: around) the rotation axis 26 such that the X-ray source 12 and the X-ray detector 14 perform a scan motion and an object 32 on the breast support 18 is radiated from different angular directions. The axis 26 can be a real (physically existing) axis or a virtual axis.

It must be noted that the X-ray radiation 16 is schematically indicated and does not relate to the actual size of a fan-like X-ray beam.

A motion adapting mechanism 34, not further shown in detail in FIG. 1, is provided that, during the scan motion, moves the X-ray detector 14 along an adapted trajectory 36 that follows the breast support surface 20. Preferably, the adapted trajectory 36 is in alignment with the breast support surface 20.

Figure 2:
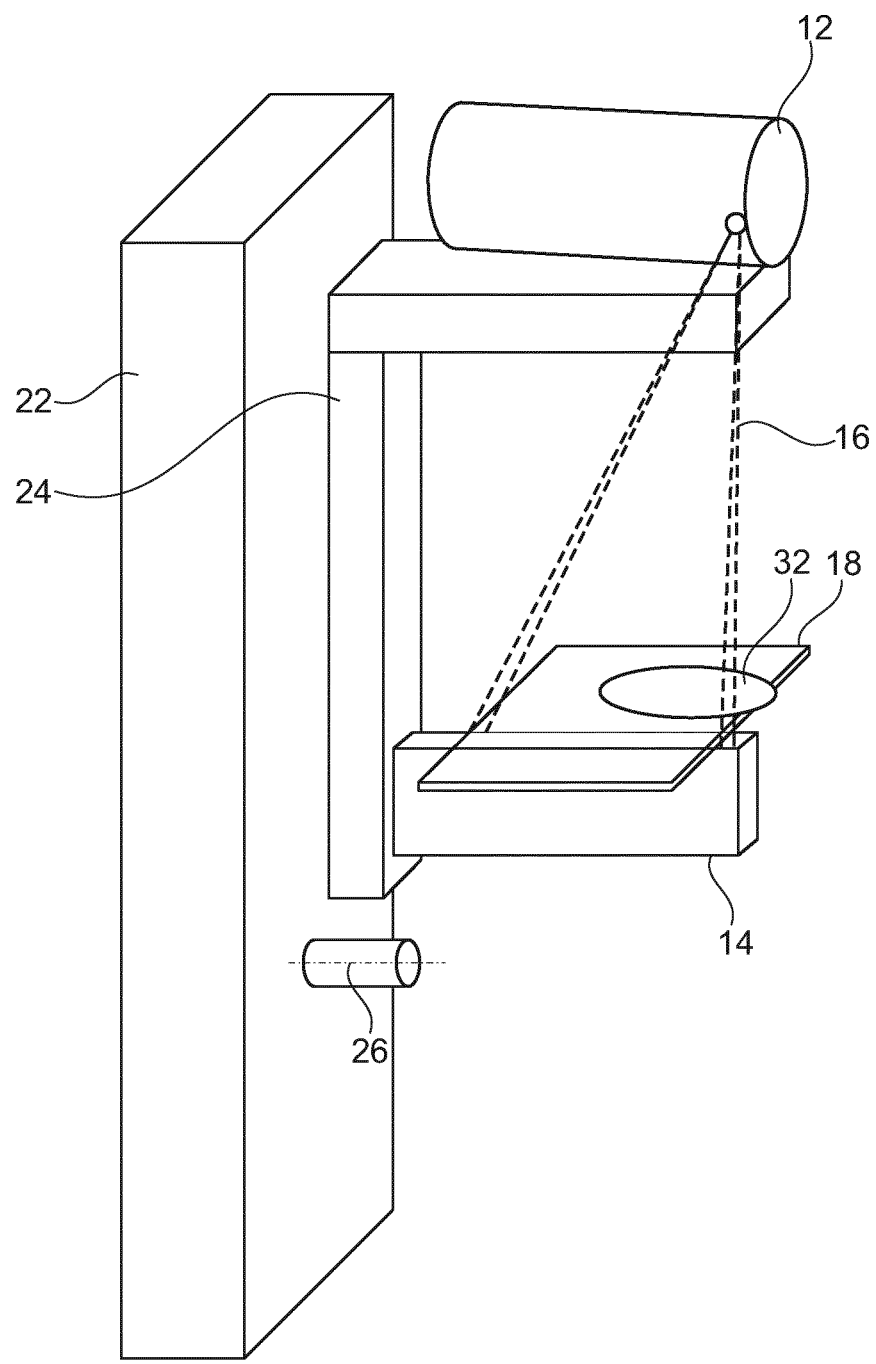
FIG. 2 shows a perspective schematic illustration of another example of a mammography X-ray imaging system.

FIG. 2 shows a perspective view of the schematic setup shown in FIG. 1. The breast support 18 with the breast support surface 20 (see FIG. 1 or FIG. 3) is shown like a flat tablet-like arrangement. Further, the object 32, for example a breast, is schematically indicated. The X-ray source 12 radiates the X-ray radiation 16 towards the detector 14 arranged below the breast support 18. The X-ray source is mounted to the scan arm 24, to which also the detector is attached. By providing the scan arm to be swivelling about the rotation axis 26, be it a concrete implementation of a rotation axis or a virtual rotation axis, the object on the breast support 18 can be radiated from different angular directions, since a relative motion is provided between the object and the radiation from the X-ray source 22.

Before going into details of different embodiments, some further explanations are provided.

The "X-ray source" is also referred to as X-ray source arrangement, or source. The X-ray source is provided for generating X-ray radiation to radiate an object, e.g. a breast arranged on the breast support.

The "X-ray detector" is also referred to as X-ray detector arrangement, or detector. The X-ray detector is provided for detecting the X-ray radiation that is radiated by the X-ray source after illumination, or radiating, and thus passing the object.

The "support structure" is also referred to as a base structure, or stand or frame that stands on the floor. The support structure provides the load bearing, i.e. the support structure supports the scan arm. For example, the support structure may be provided as a standing support structure in order to transfer the load to a floor construction. The support structure may also be provided as a suspending support in order to transfer the load to a ceiling structure in a hanging manner.

The "breast support" is also referred to as breast support arrangement, or object support. The breast support relates to a support for holding, i.e. supporting the breast of a patient during X-ray image acquisition. The breast support provides a (lower or) base surface for supporting the breast, which surface is also referred to as breast support surface. The breast support can comprise an upper surface for holding the breast from atop, e.g. for acting on the breast with an adjustable pressing force. The breast support can be provided as two breast compression paddles. The breast support can be adaptable in height. Alternatively, or in addition, the distance between the lower and the upper part of the breast support can be adaptable to different breast sizes and different elasticities of a breast. In an example, the breast support is attached to the support structure.

The "scan arm" relates to an arm-like structure that can be pivoted (or rotated about a rotation axis) for providing the scan motion in order to provide a plurality of X-ray images of an object, i.e. a breast, arranged on the breast support. The scan arm thus provides the moving support for the X-ray source and the X-ray detector. In an example, the scan arm is extending vertically.

In an example, the scan arm is mounted to the support structure directly. In another example, the scan arm is indirectly mounted to the support structure by a secondary structure, or sub-structure, that is movably mounted to the support structure. The secondary sub-structure thus provides an adjustment of the field of movement of the scan arm. For example, the sub-structure may provide a rotation adjustment of e.g. approximately 0° to 180°. The sub-structure may also provide a translation adjustment, e.g. up and down to find different positions for different examination angles and for different patients length.

In an example, the sub-structure is tilted towards or away from the patient, e.g. up to 10°.

In an example, the sub-structure is tilted by up to 90° towards or away from the patient, e.g. up to 10°. As an option, the X-ray imaging of a breast is thus also possible for patients arranged on a bed or other horizontal patient support. Such imaging may be used during interventions when a patient cannot stand up. This is also referred to as prone tables where a scan arm is arranged underneath a (patient) table or patient support. For example, the complete mammography X-ray imaging system is arranged e.g. tilted in any direction and also horizontally.

The sub-structure is also referred to as a C-arm structure, comprising a chassis or C-arm house, and an interface to the scan arm. However, it must be noted that the term "C-arm" in this context shall not be understood as a C-arm structure in an X-ray full body examination apparatus where a patient can be arranged on the table and a C-arm is provided for scanning movement around the patient.

The terms "vertically", "horizontally", "up or down" and "left and right" or others like "front and back" relate to an arrangement of the system during normal operation, when the patient is arranged in an upright position, at least with the upper part of the body, i.e. the breast area, such as when sitting or standing for the purpose of the image acquisition. It must be noted that due to the rotation adjustment mentioned above, also a respective different arrangement of the complete structure can be provided, and the terms like "vertically", "horizontally", "above", "below" etc. would then have to be so-to-speak translated in different directions. Hence, the terms "above", "below" etc. relate to an arrangement of the system in an operation mode where the patient is standing or sitting in an upright manner during image acquisition. The term "upwardly extending" or "vertically extending" relates to an extension in an approximately vertical direction, including deviations in a range of approximately +/−45°. In general, the scan arm is provided for holding an X-ray source above the breast and for holding an X-ray detector below the breast in order to provide a radiation of the breast in a way that the breast can be identified on the image. During operation, the scan arm changes its orientation due to the rotation or swivel motion about the rotation axis.

The term "swivel" relates to a pivoting scan motion. In an example, the swivelling scan motion is provided about a fixed rotation axis or about a rotation axis that moves during the scan motion. In an example, the rotation axis is a virtual rotation axis. During the scan motion, the rotation axis may be fixed or may also move along an axis-trajectory. In another example, the rotation axis is a rotational bearing providing the rotation axis.

The "rotation axis" relates to a geometric axis, around which the pivoting motion or movement takes place. The "rotation axis" can relate to a physical bearing providing an axis of rotation, or rotation axis. The "rotation axis" can also relate to a virtual rotation axis.

The rotation axis can also be referred to as point of rotation or rotation point. By providing the pivot point, or rotation axis, below the breast support, the scan arm can provide a synchronized, or interrelated, X-ray detector and X-ray source movement. Since the X-ray detector is arranged on the scan arm closer to the rotation axis, the X-ray source performs a larger movement, i.e. the X-ray source is moved along a longer source-trajectory 47, i.e. on a longer track of movement.

In an example, the scan motion is provided as a circular motion.

In another example, the scan motion is provided as a circular motion of the scan arm combined with a simultaneous translational displacement.

In another example, the scan motion is provided as a substantially linear motion or translation of the scan arm combined with a simultaneous rotational movement. In an example, the pivoting movement of the scan arm provides a scan angle in the range of approximately +/−5° to +/−30°, e.g. approximately +/−17°. Hence, the object is radiated by X-ray radiation from different angles covering such angular range. For example, a total movement of about +/−17° is provided, which creates a specific image width. In one example, an angle for tomosynthesis is provided that is a sum of angles between a first and a last detector line plus the angle of rotation to have a point in the object radiated, i.e. "imaged" by the first and the last line of the detector. The tomosynthesis angle can in this case also be described as determined by the height position of the rotation axis compared to the patient support, as well as by the width of the detector.

In an exemplary concept, constructive measures are taken that force the detector following the patient support on a decided offset distance to create just enough safety distance to not having any collision of the moving detector with the not-moving other parts.

In another exemplary concept, a movement of supporting parts is provided that result in the detector following the patient support on a decided offset distance to create just enough safety distance to not having any collision of the moving detector with the not-moving other parts. The detector itself still moves on a circular track in relation to its support structure, but since the additional movement of the supporting parts is provided, which also leads to an indirect movement of the detector, the result is a relative movement of the detector to the breast support that is "balanced" at least partly in view of the rotational movement vector components of the swivelling movement.

In an example, the motion adapting mechanism reduces, i.e. minimizes a change of a distance between the X-ray detector and the breast support during the scan arm motion.

In an example, the motion adapting mechanism at least partly "balances" the change of a distance between the X-ray detector and the breast support during the scan arm motion due to the swivelling basic character of the scan motion.

In an example, the motion adapting mechanism is a motion reduction mechanism that reduces the rotational movement vector component by providing an offset during the pivoting scan motion.

The term "balancing" relates to counteract a movement that would otherwise appear. As an example, the counteracting is a constructional provision that adapts the motion such that the X-ray detector moves along the adapted trajectory that follows the breast support surface. The "balancing" can also be referred to as to "make up for" the movement of the scan motion. The "balancing" relates to a (virtual) compensation of the scan movement in order to align the movement of the detector to the breast support surface. This compensation must not be taken as what is known as motion compensation applied e.g. during X-ray imaging to compensate for patient movement during the image acquisition, for example, breathing motion or heartbeat motion.

In an example, the motion adapting mechanism offsets the detector in a direction toward or away to the breast support surface during the swivelling motion of the scan arm.

In an example, the motion adapting mechanism is provided such that, during the scan motion, the X-ray detector is offset in a vertical direction, i.e. away or against the breast support surface, for at least partly balancing the change of the distance between the X-ray detector and the breast support during the scan arm motion.

The "adapted trajectory" is a way of movement of the detector that is at least a flattened trajectory, with respect to the rotation axis. The adapted trajectory can be provided as a flat trajectory, such as an approximately linear or substantially linear trajectory. The adapted trajectory can be linear or slightly curved. The trajectory of the detector is also referred to as trajectory.

The term "follows the breast support" relates to a trajectory that is substantially aligned to the breast support surface such that the gap or distance between detector and object is minimized. During the scan motion, the detector is moved below the breast support surface in such a way that the detector movement is aligned to the breast support surface. The detector's movement direction is oriented to the direction of the breast support surface extension with regard to the scan direction. Although the scan motion is basically a swivelling or pivoting motion, the detector moves along, i.e. below, the breast support to keep a substantially constant distance to the breast support surface.

In an example, the distance is kept at a minimum during a major part of the scan motion, e.g. during at least approximately 50% of the scan motion, e.g. during 75%, or 80%, or more %. In an example, the distance is kept at a minimum during the complete scan motion. Generally, the term "approximately" relates to a deviation of up to +/−20%, e.g. +/−10% or +/−5%.

In an example, the trajectory provides for a safety distance and is adapted to the surface (for supporting the breast) that may deflect more in the centre, i.e. "bend" caused by the weight of the breast.

In an example, during the scan motion, the breast support arrangement remains fixed in relation to the support structure.

The alignment relates to an aligned orientation or direction, i.e. next to each other or beside each other, but not coinciding or overlapping.

For example, the alignment comprises:
i) a maximum deviation along the length of +/−5% with respect to a distance between the adapted trajectory and the breast support surface.

In an example, an alignment is provided such that a distance between patient support and detector will be approximately maximum 10 mm, e.g. maximum 5 mm, or maximum 2 mm, with respect to the maximum side positions of the scan arm. In an example, in the centre position, the distance between patient support and detector will be approximately maximum 15 mm, e.g. maximum 7 mm.

In an example, the distances along the scan motion will provide a curve comprising of two curves that are crossing each other, giving a distance that does not change in a linear way. This may be caused by the detector having a certain width, even when provided as a line detector such that the two corner portions of the detector are getting closer to the support surface as the detector is moving during the scan motion.

In an example, the distance is kept as small as possible, e.g. with a maximum variation within a range of 1 mm to 20 mm, e.g. 1 to 10 mm.

For example, the alignment comprises:
ii) a maximum deviation of +/−5° with respect to an inclination of the adapted trajectory to the breast support surface.

For example, the adapted trajectory is substantially parallel to the breast support surface. In an example, the breast support surface is a horizontal surface, and the adapted trajectory is a flattened or linear trajectory.

In an alternative example, the breast support surface is a concave structure providing a recess to support the breast, and the adapted trajectory is an adapted trajectory with a similar concave structure (see below).

The term "flattened" relates to a trajectory that has at least a larger radius than a respective rotational movement vector of the swivelling scan arm motion.

In an example, the concave structure provides a concavity of approximately maximum 15%, i.e. a provided recess is maximum 15% of the surface's width. For example, a maximum of approximately 10% or 5% is provided. In an example, an average width of approximately 100 to 400 mm is provided, e.g. 200 to 300 mm, such as approximately 260 mm. A curved profile with approximately up to 20 mm height is provided, e.g. maximum 15 mm, for example 10 mm or 5 mm.

In an example, the X-ray detector moves in a linear manner. In another example, the X-ray detector moves in a substantially linear manner. For example, the X-ray detector moves in a slight curved manner.

In the concave support surface, in one example, the adapted trajectory relates to a linear trajectory. In another example, the trajectory is approximately parallel to the concave support surface.

Figure 3:
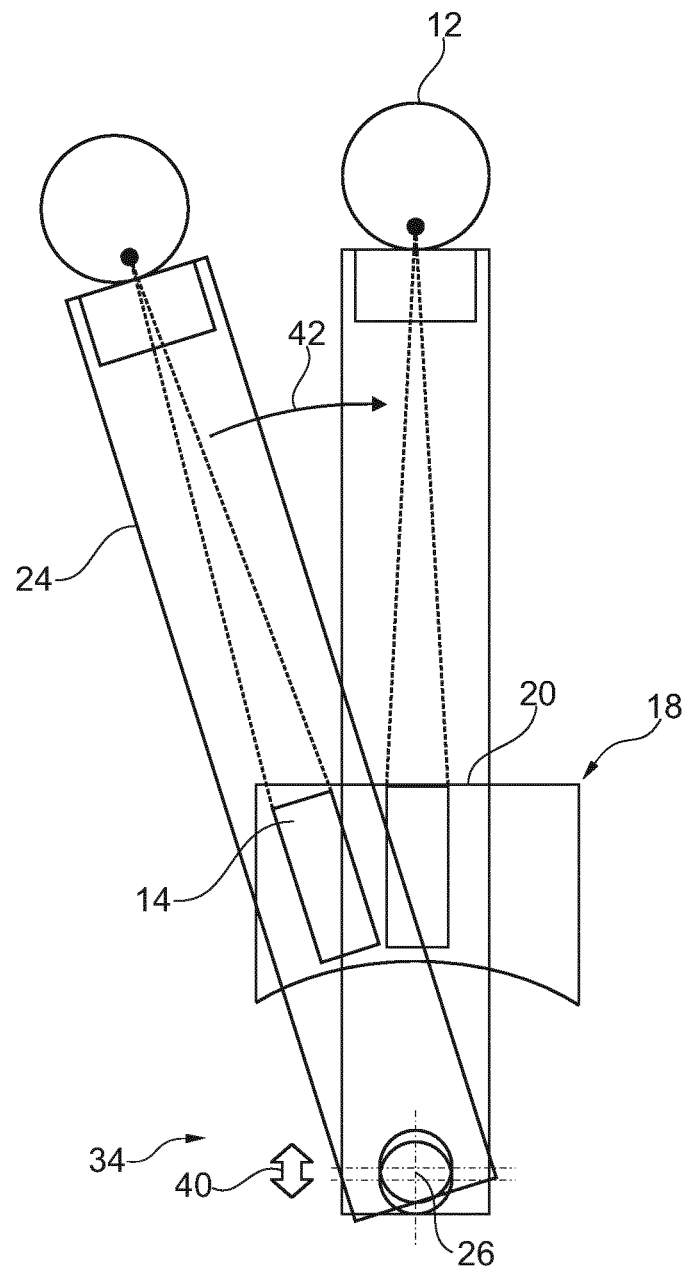
FIG. 3 shows an example of a moving mechanism for providing an adapted trajectory for a detector.

FIG. 3 shows a further example in a schematic setup, and the motion adapting mechanism 34 provides a vertical displacement, indicated with double arrow 40, of the rotation axis 26, and the scan arm remains fixed in relation to the rotation axis in radial direction. By providing the vertical displacement, the swivel motion, indicated with an arrow 42, becomes so-to-speak flattened and it is possible to move the X-ray detector 14 in a more or less linear manner along an adapted trajectory that follows the breast support surface 20.

In an example, during the scan motion, the rotation axis 26 (either as virtual or as real axis) remains fixed in respect to a direction transverse to the scan arm's extension, e.g. in the horizontal direction when arranged in a vertical manner as shown. In case of a tilted or inclined arrangement of the system, the fixation of the axis' location relates to a respective other direction.

In another example, during the scan motion, the rotation axis 26 (either as virtual or as real axis) is moved in respect to a direction transverse to the scan arm's extension.

Figure 4:
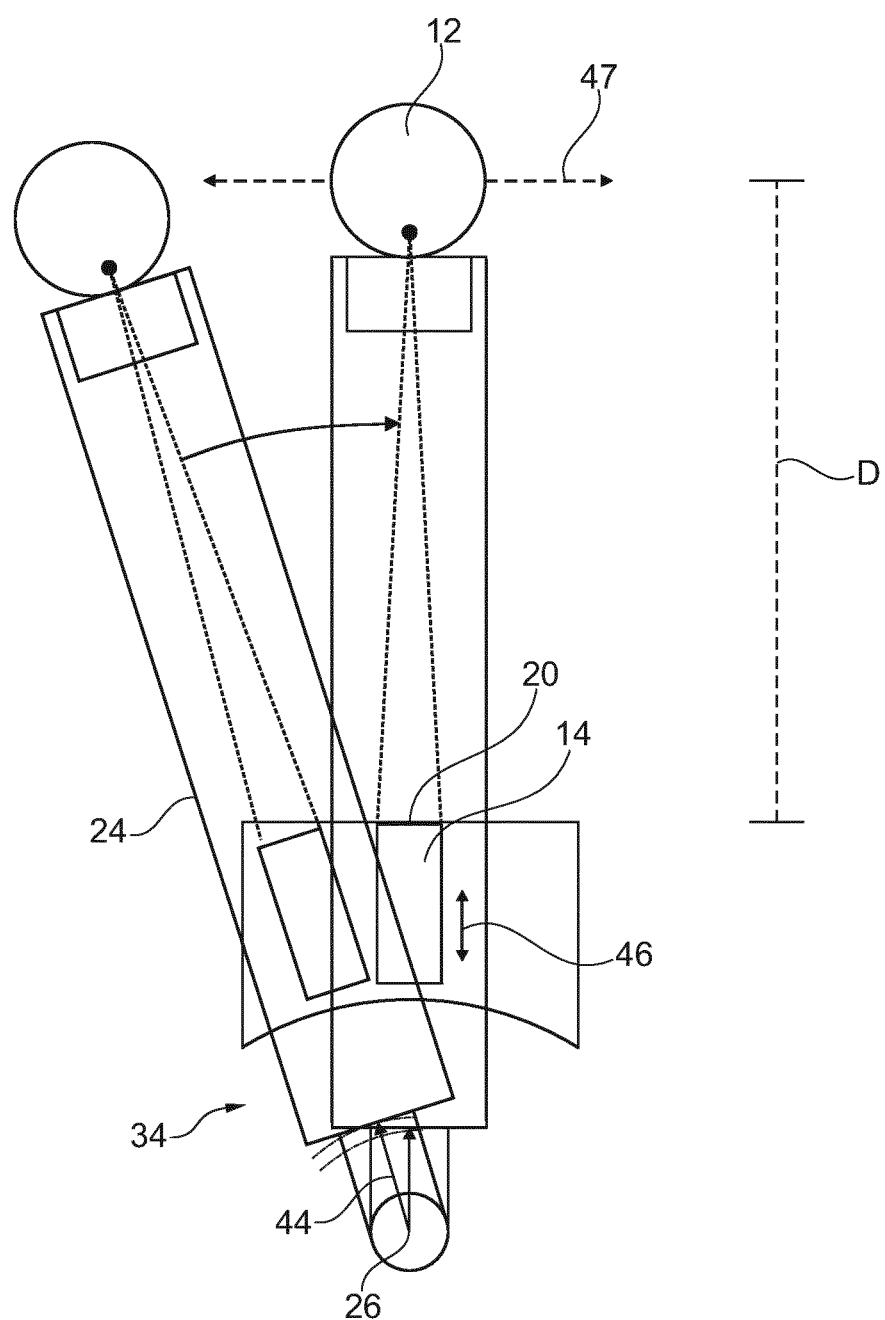
FIG. 4 shows a further example of a motion adapting mechanism in a schematic setup.

FIG. 4 shows a further example, where the rotation axis 26 remains fixed during a scan, and the motion adapting mechanism 34 displaces the scan arm 24 in relation to the rotation axis 26 in radial direction, as indicated with arrow 44. The result is, as before, that the X-ray detector 14 moves along an adapted trajectory 36 that follows the breast support surface 20.

The term "radial direction" relates to a relative distance to the rotation axis, i.e. along the line of the radius.

Hence, as an example, it is provided that the X-ray detector 14 is moved along the adapted trajectory 36 that follows the breast support, in which the motion adapting mechanism 34 provides a radial displacement, indicated with double arrow 46, of the X-ray detector 14 in relation to the rotation axis 26 during the scan motion, as indicated as an option in FIG. 4.

The radial displacement may also be referred to as radial movement.

In a further example, in addition or alternatively, the motion adapting mechanism provides a radial displacement of the X-ray source in relation to the rotation axis during the scan motion.

In one example, the X-ray source is fixed to the scan arm, and the X-ray detector is moved along the scan arm (in radial direction) during the scan motion.

According to another example, indicated in FIG. 4 as a further option, which is also provided in combination with other options described in relation with other figures, the X-ray source 12 and the X-ray detector 14 are provided in a fixed relative distance D to each other during operation. The motion adapting mechanism 34 moves the X-ray source 12 along an adapted source trajectory, indicated with dotted arrow 46 that is adapted in the direction of the breast support surface 20.

In an example, the motion adapting mechanism moves the X-ray source 12 and the X-ray detector 14 along the adapted trajectories following the breast support surface in a synchronized motion.

In another example, the motion adapting mechanism 34 moves the X-ray source 12, the collimator (see further below) and the X-ray detector 14 along the adapted trajectories following the breast support surface in a synchronized motion.

In an example, an actuating mechanism is provided that provides an actuation of the scan arm, and thus the X-ray detector 14 and the X-ray source 12, away from or toward/against the rotation axis 26 in a radial manner during the scan motion.

In an example, the X-ray detector 14 and the X-ray source 12 are moved together as one set.

According to a further example, shown as an option with a dotted line in FIG. 1, a pre-collimator 48 is provided that is mounted to the scan arm 24. During operation, the motion adapting mechanism moves the pre-collimator 48 along an adapted collimator trajectory that follows the breast support surface.

In an example, the pre-collimator trajectory is aligned to the breast support surface, however, with a larger distance to the breast support surface than the detector's trajectory, since the breast is arranged between the breast support surface and the collimator.

In an example, an upper breast holding surface is provided, e.g. a compression paddle (not further shown).

In an example, the motion adapting mechanism 34 moves the X-ray detector 14 and the pre-collimator 48 along the adapted trajectories following the breast support surface.

In an example, a secondary guidance support is provided for guiding the collimator. The secondary guidance is provided as an arcuate guide support forming a curve with a larger radius than the distance to the rotation axis of the scan arm, or as a linear horizontal guide support (see also below).

In an example, the motion adapting mechanism 34 moves the collimator 48 and the X-ray detector 14 along the adapted trajectories following the breast support surface in a synchronized motion.

For example, the X-ray detector 14 is moved parallel to the breast support surface. In another example, the X-ray detector is moved with reduced distance variation compared to the scan arm rotational movement.

With respect to the following of the trajectory, i.e. the alignment, it is also referred to the above in relation with the detector's trajectory.

In an example, during the scan, the X-ray detector travels near the patient support, i.e. the breast support.

In an example, the breast support comprises an upper breast holding element, and the breast support surface and the upper breast holding element enclose a volume having a flat upper and a flat lower shape. The motion adapting mechanism provides that the X-ray detector follows the flat lower shape. In an example, where the collimator is provided, the motion adapting mechanism also provides that the collimator follows the flat upper shape. As mentioned above, the upper breast holding element can be provided as compression paddle.

The volume can also be referred to as rectangular box shaped imaging or scanning volume.

In an example, the X-ray detector and the collimator are moved together as one set.

In another example, the X-ray detector, the X-ray source and the collimator are moved as one set.

Figure 5:
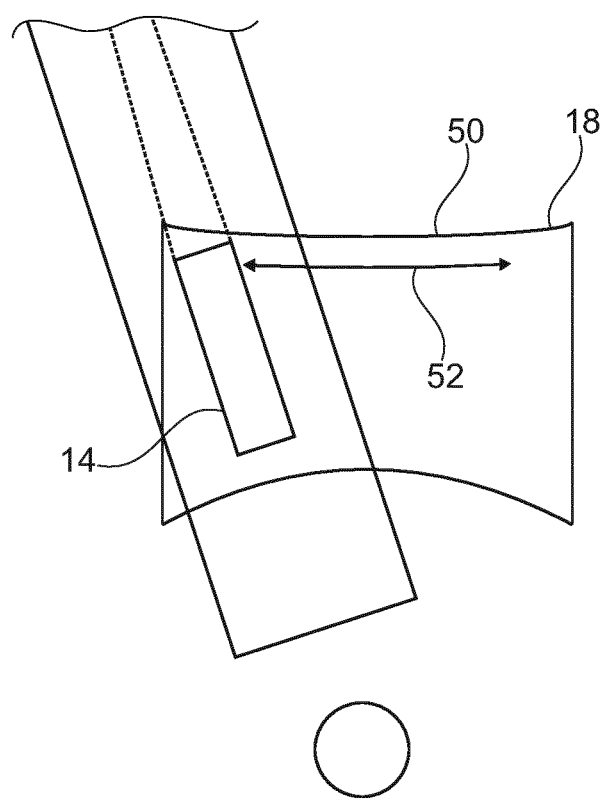
FIG. 5 shows a breast support with a concave breast support surface as an example.

Before turning to the further embodiments having at least one guiderail, it is referred to FIG. 5.

In FIG. 5, the surface of the breast support 18 is provided as a concave surface 50 for supporting a breast. During the scan motion, the X-ray detector 14 moves along an arc trajectory 52, which is an arc having a virtual rotation axis arranged above the breast support 18, and thus opposite to the swivelling motion and its rotation axis below the breast support.

According to an example, not further shown in detail, the X-ray detector 14 is a line-detector comprising a plurality of strip detector segments. For example, 21 detector lines are provided.

In another example, the collimator is a pre-breast collimator. For example, the collimator comprises a plurality of collimator slits. In one example, the collimator slits are provided corresponding to the detector lines. For example, the X-ray detector is a silicon-strip detector. The strip-pitch may be provided in the range of approximately 10 to 500 micrometres, e.g. approximately 50 micrometre.

In a further example, although not further shown, the X-ray detector is a photon-counting detector.

Turning to the following figures, an example is provided, in which the motion adapting mechanism 34 comprises at least one guiderail with an extension direction adapted to the breast support surface. The at least one guiderail provides that the X-ray detector follows the breast support surface during the scan motion.

The term "adapted" relates to a direction that is at least less curved than a circular trajectory around the rotation axis. In one example, at least one horizontal primary guiderail is provided for a sliding support of the X-ray detector during the swivelling scan motion. The guiderail is adapted to follow the breast support surface for vertical alignment of the detector during the scan motion such that the distance between the detector and the breast support surface is kept substantially constant during the scan motion.

The guidance can be a horizontal guiderail, or a curved guiderail, but with a curvature radius that is larger than the respective distance to the rotation axis.

During the scan motion, the X-ray detector is thus moved to balance a circular trajectory that would occur during the pivoting motion, such that an effective trajectory of the X-ray detector is flattened, i.e. the trajectory is provided such that the distance between the X-ray detector and the breast does change only minimally during the scan motion. In an example, the effective trajectory is a substantially flat, e.g. Horizontal line.

FIG. 6A shows an example, in which the motion adapting mechanism 34 comprises two guiderails 54. One of the guiderails is provided above the breast support 18 as an upper guiderail 58, and another one of the guiderails is provided below this upper guiderail 58 as a lower guiderail 56. At least one of the guiderails 54, i.e. at least one of the lower guiderail 56 or the upper guiderail 58, provides the swivelling motion of the scan arm about a virtual rotation axis and at least another one of the guiderails provides that the X-ray detector 14 follows the breast support surface 20.

The two guiderails can be referred to as first and second guiderail.
The guiderail providing that the X-ray detector follows the breast support surface is also referred to as the leading guiderail, or primary guiderail. The other guiderail is also referred to as the secondary guiderail.

In an example, a bearing point, or a pivot point, i.e. a point of rotation, is physically not present. The guiderails so-to-speak virtually form such rotation point, fixed or moving.

According to an example, shown in FIG. 6A as an option, one of the guiderails is a curved guiderail that provides the swivelling motion of the scan arm about a virtual rotation axis, and the other one of the guiderails is an at least less-curved guiderail that provides that the X-ray detector follows the breast support surface.
The term "less-curved" relates to a curve having a radius that is at least twice the radius of the other curve.

In this example, the less-curved guiderail is the leading guiderail.
For example, FIG. 6A shows that the upper guiderail 58 is the curved guiderail and the lower guiderail 56 is the less-curved guiderail, for example a flattened or straight guiderail. Two movable bearings 60 for the scan arm are provided to move along the upper, curved guiderail for swivelling the scan arm 24 during the scan motion. The two movable bearings 60 are having a fixed distance to each other in direction of the guiderail. The lower guiderail provides for the carrying of the scan arm and for guidance of the X-ray detector to follow the adapted trajectory.

FIG. 6B shows the example of FIG. 6A wherein the swivelling motion has taken place to the left in the figure. As can be seen, the X-ray detector is kept at a minimum distance to the breast support 18.

In an example, the lower guiderail is slightly curved, and in another example, the lower guiderail is linear, i.e. Horizontal, as indicated in FIG. 6A and FIG. 6B.

In this example, the less-curved lower guiderail is the leading guiderail.

The two movable bearings 60 are provided as wagon-like bearings or supports.

Figure 7B:
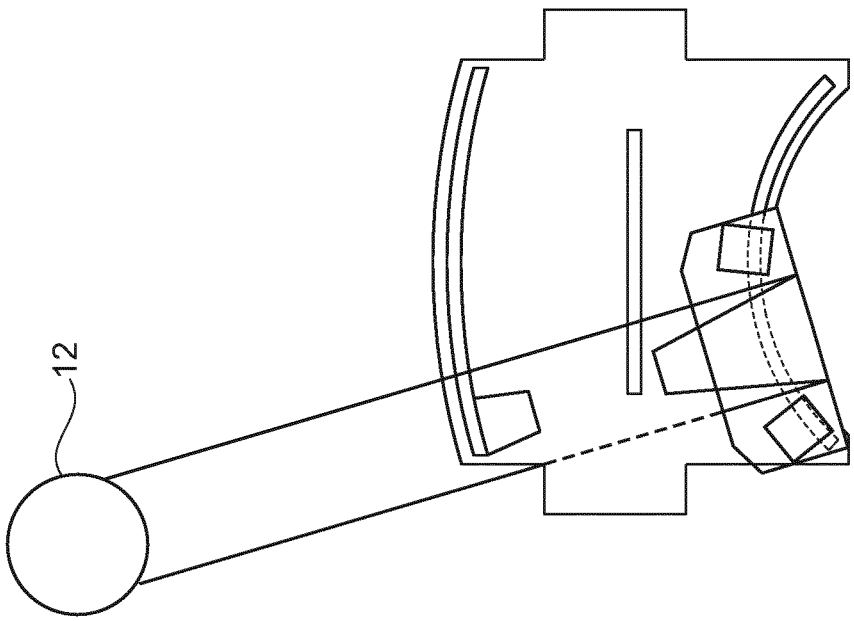
FIG. 7A and FIG. 7B show a still further example of a mammography X-ray imaging system.
Figure 7A:
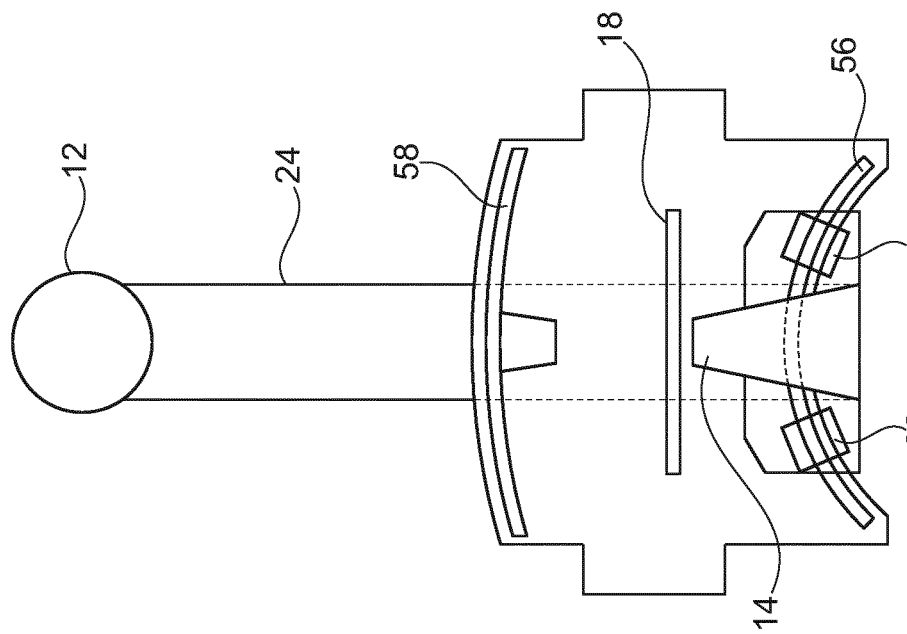

FIG. 7A and FIG. 7B show an example where the upper guiderail 58 is the less-curved guiderail, and the lower guiderail 56 is the curved guiderail. Two movable bearings 62 for the scan arm are provided to move along the lower, curved guide rail for swivelling the scan arm 24 during the scan motion. The two movable bearings 62 are having a fixed distance to each other in direction of the guiderail. The upper guiderail 58 provides for the carrying of the scan arm, and for guidance of the X-ray detector to follow the adapted trajectory, as can be seen by comparing FIG. 7A with FIG. 7B.

In a further example, the upper guiderail is slightly curved as indicated. In another example, the upper guiderail is linear, i.e. Horizontal.

In this example, the less-curved upper guiderail is the leading guiderail.

FIGS. 8A and 8B show a further example, where a third guiderail 64 is provided between the lower guiderail 56 and the breast support surface 20. Still further, also the upper guiderail 58 is shown.

The third guiderail 64 provides for the carrying of the scan arm, and for guidance of the X-ray detector 14 to follow the adapted trajectory. The two movable bearings 62 for the scan arm are provided to move along the lower, curved guiderail for swivelling the scan arm during the scan motion. The two movable bearings 62 are having a fixed distance to each other in direction of the guiderail. The upper guiderail 58 provides for additional support of the scan arm 24. A pre-collimator 66 is arranged between the X-ray source 12 and an object, indicated with circle 68.

It is noted that the pre-collimator 66 can also be provided as an option for the other examples shown in the other figures, and also for the other examples that are further mentioned in the description.

In a further example (not shown), the upper guiderail provides for guiding the pre-collimator 66.

In an example, the pre-collimator 66 is supported by bearings that are arranged to slide on a separate guide rail. This allows an adaption of the collimator's trajectory.

In another example, the pre-collimator 66 is supported by the scan arm and moves together with the scan arm in the same manner, e.g. parallel to an X-ray source, when this is fixedly mounted.

In still another example, the pre-collimator 66 is supported by the scan arm, but a pre-collimator motion adapting mechanism is provided for achieving an adapted pre-collimator trajectory in order to also move the pre-collimator such that it follows the support surface.

In an example, the motion adapting mechanism also causes the movement of the collimator along the adapted collimator-trajectory that follows the breast support surface. For example, the collimator is moved either directly when moved actively, or indirectly when being arranged fixedly to the X-ray detector and/or X-ray source.

For example, the detector is arranged in a fixed position in ration to X-ray detector and X-ray source and moves together with these during X-ray imaging.

In another example, collimator is provided that moves independently, however along an adapted collimator-trajectory. As shown in FIG. 8B, also the pre-collimator 66 is moved along an adapted trajectory to keep a minimum distance to the object to be radiated.

FIGS. 9A and 9B show a further example, where the two guiderails are provided as linear guiderails 70. Sliding bearings 72 are provided for each guiderail. The swivel motion of the scan arm, as indicated in FIG. 9B with swivelling arrow 74, is provided by a synchronized movement of the sliding bearings 72 along the upper and lower guiderails 70. One of the two guiderails provides that the X-ray detector follows the breast support surface 20.

The guiderail, which is providing that the X-ray detector follows the breast support surface in an example, is the leading guiderail.

The two guiderails, e.g. the first and the second horizontal guide for supporting the scan arm, are provided offset in a vertical direction.

The scan arm is movably mounted to the horizontal guides with a first and a second movable bearing, e.g. a slideable support. The first and the second movable bearing are moved along the respective horizontal guiderail with different speeds to provide a combined movement of the scan arm, comprising translational movement of the scan arm in relation to the horizontal guides, and rotational movement of the scan arm in relation to a virtual rotation axis, which may move or stay fixed during the scan arm motion.

Figure 10:
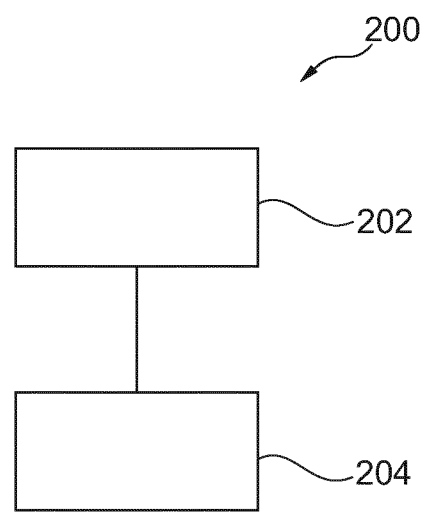
FIG. 10 shows basic steps of an example of a method for providing X-ray mammography X-ray imaging data.

In FIG. 10, an example of a method 200 for providing mammography X-ray image data for tomosynthesis mammography is provided. The method comprises the following steps.

In a first step 202, also referred to as step a), an object of interest is arranged on a breast support surface of a breast support.

In a second step 204, also referred to as step b), the object is scanned with radiation provided from an X-ray source towards an X-ray detector. The X-ray source and the X-ray detector are mounted on an upwardly extending scan arm. The X-ray source is mounted on the scan arm above the breast support and the X-ray detector is mounted on the scan arm below the breast support. The scan arm is movably mounted to a support structure to perform a swivelling motion about a rotation axis located below the breast support.

During the scanning in step b), the scan arm is swivelling about the rotation axis such that the X-ray source and the X-ray detector perform a scan motion and the object on the breast support is radiated from different angular directions.

During the scanning in step b), a motion adapting mechanism is moving the X-ray detector along an adapted trajectory that follows the breast support surface.

During the scanning in step b), X-ray radiation is detected by a detector after having passed through the object.

Figure 11:
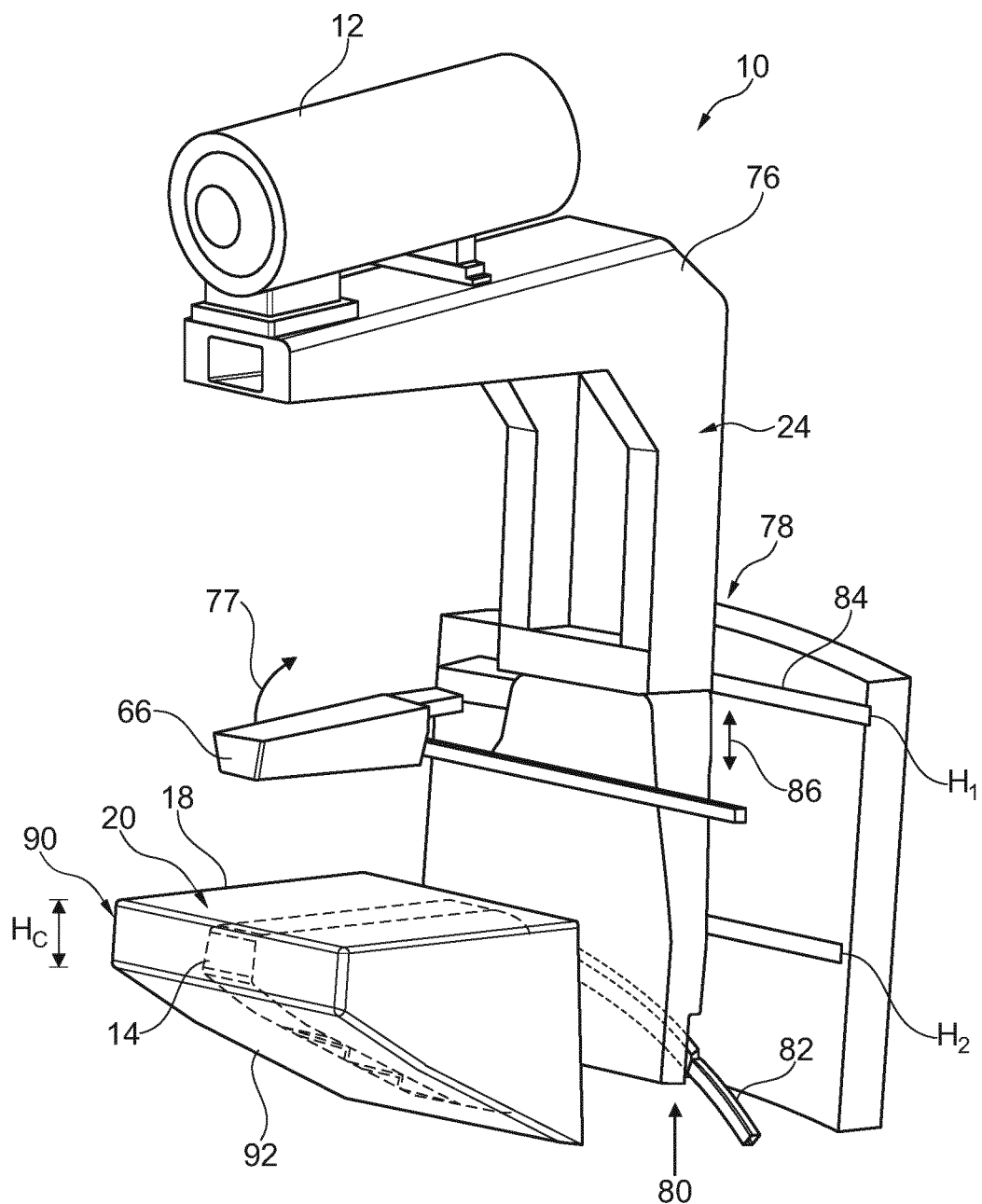
FIG. 11 shows another example of the mammography X-ray imaging system.

FIG. 11 shows a perspective view of another example of the mammography X-ray imaging system 10. The X-ray source 12 is mounted on top of a cantilevering portion 76 of the scan arm 24.

X-ray radiation (not further indicated in FIG. 11) is generated by the X-ray source 12 in direction of the X-ray detector 14. As an option, the X-ray radiation passes the pre-collimator 66 before radiating the object, i.e. the breast, which is arranged on the breast support surface 20 of the breast support 18.

The pre-collimator 66 is connected to the scan arm 24. As an option, the pre-collimator 66 can be moved, e.g. pivoted (as indicated with arrow 77), upwards to facilitate the process of arranging the patient's breast. During imaging, the pre-collimator 66 is in the lowered position, i.e. in the shown position.

The scan arm 24 is movably mounted to the support structure 22, which support structure 22 can also be referred to as chassis. The scan arm 24 is supported by two upper bearings 78 (not shown in detail) and two lower bearings 80, i.e. an upper pair and a lower pair of bearings.

Each pair comprises two bearings arranged in a fixed, i.e. constant distance. Instead of the upper pair, also one, or more than two, e.g. three, four, five or more bearings can be provided. Instead of the lower pair, also more than two, e.g. three, four, five or more bearings can be provided.

The lower support is provided in form of a curved linear guiderail 82. During the scan motion, the two lower bearings 80 of the lower pair guide along the curved guiderail and thus cause the pivoting motion of the scan arm. The bearings can be provided as curved linear ball guides. For example, the curved guiderail 82 covers an angle of approximately 90°. The distance between the two lower bearings may be provide as a ¼ (one quarter) of the angle's width The upper support is provided in form of a straight linear guiderail 84. During the scan motion, the two upper bearings 78 of the upper pair guide along the straight linear guiderail and at the same time move in relation to the extension direction of the scan arm, which extension is indicated with an arrow 86. The upper support thus holds the arrangement in place and prevents a tilting of the X-ray source towards the patient (which patient is standing so-to-speak in front of the arrangement).

In an example, the scan arm 24 can thus move vertically in respect of the support structure 22.

It is noted that the upper support can be provided at different heights, such as a first height $H_1$ or a second height $H_2$. Further, a combination can be provided, i.e. supports at both heights.

During the scan motion, the breast support 18 remains fixed in relation with the support structure 22. In other words, during operation, the scan arm 24, and with it the X-ray source and the detector move in relation to the breast.

Further, a patient support cover 90 is indicated in FIG. 11 enclosing a space, which is provided for allowing a movement of the X-ray detector 14. It is noted that such a cover or enclosure of the patient support structure is also provided for the other examples described above. Due to the adapted trajectory 24 for the X-ray detector movement, e.g. the slide scan function, which is provided according to the present invention, the height of the space needed for the X-ray detector's motion is reduced in particular in the region that is closer to the patient. Hence, the patient support cover 90 is provided with an inclined front side 92. In other words, a required height $H_c$ of the cover at the front side is reduced. During the scan motion, the patient support cover 90 remains fixed.

Figure 12:
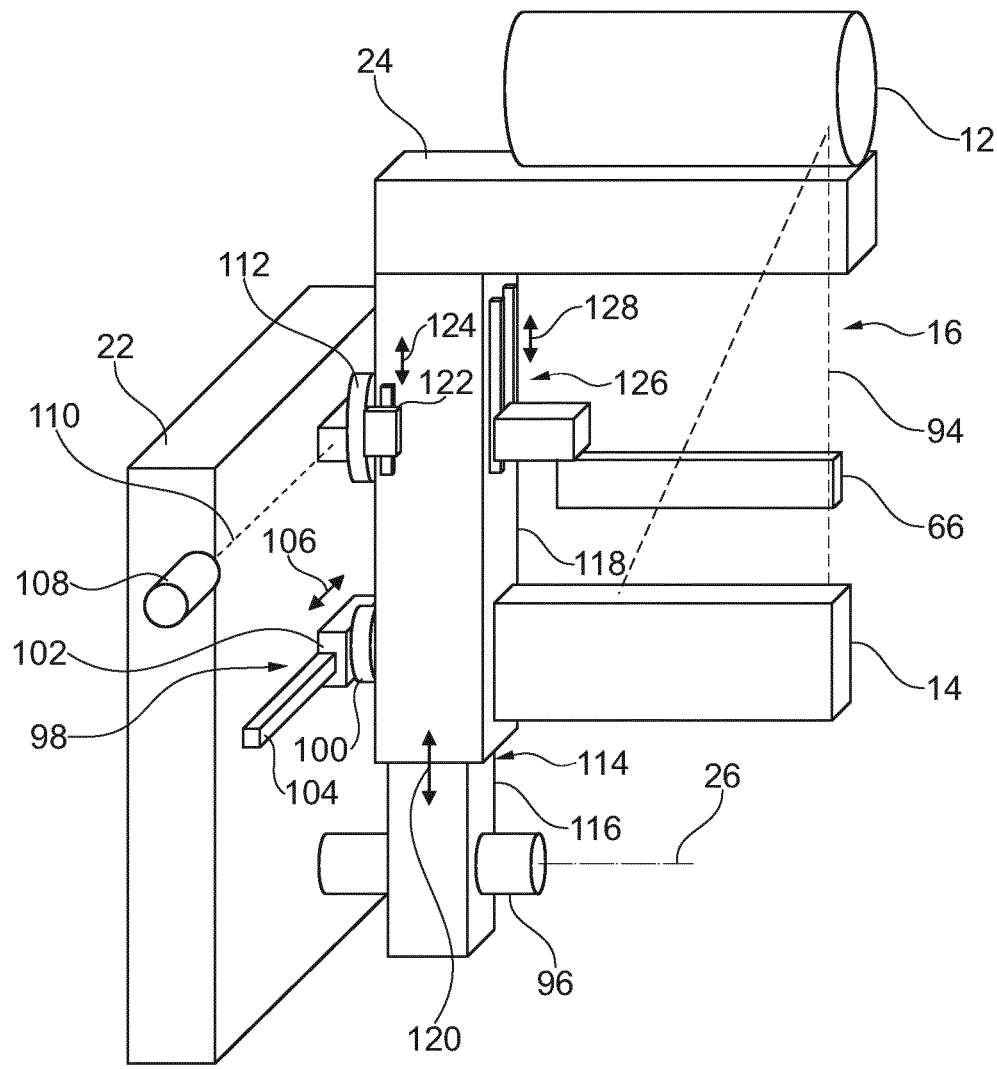
FIG. 12 shows another illustration of a basic slide scan function.

In FIG. 12, another illustration of a basic slide scan function is shown. The X-ray source 12 is supported by the scan arm 24 and is provided to generate the X-ray radiation 16, indicated with dotted lines 94, towards the X-ray detector 14. As an option, the pre-collimator 66 is indicated. An object, e.g. a breast, can be arranged between the X-ray source 12 and the X-ray detector 14. In case of a pre-collimator, the object, e.g. the breast, can be arranged between the pre-collimator 66 and the X-ray detector 14.

Figure 13:
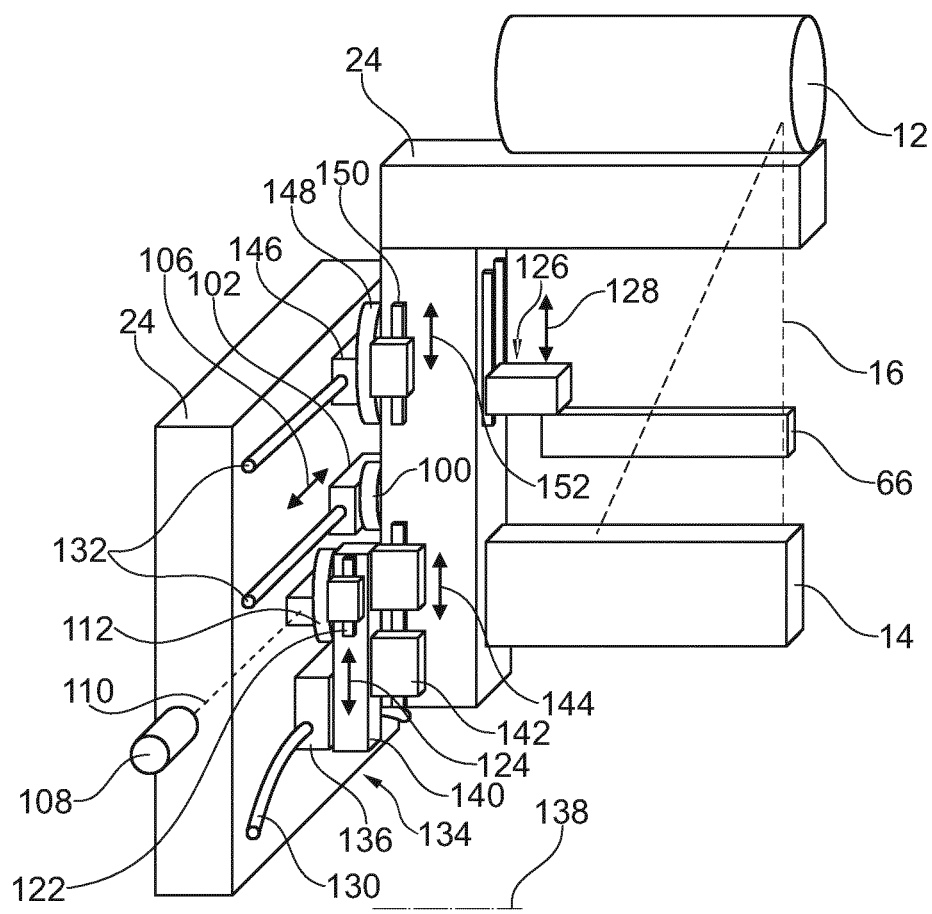
FIG. 13 shows an example of a mechanical concept with a lower curved guiderail and two upper straight guiderails.
Figure 14:
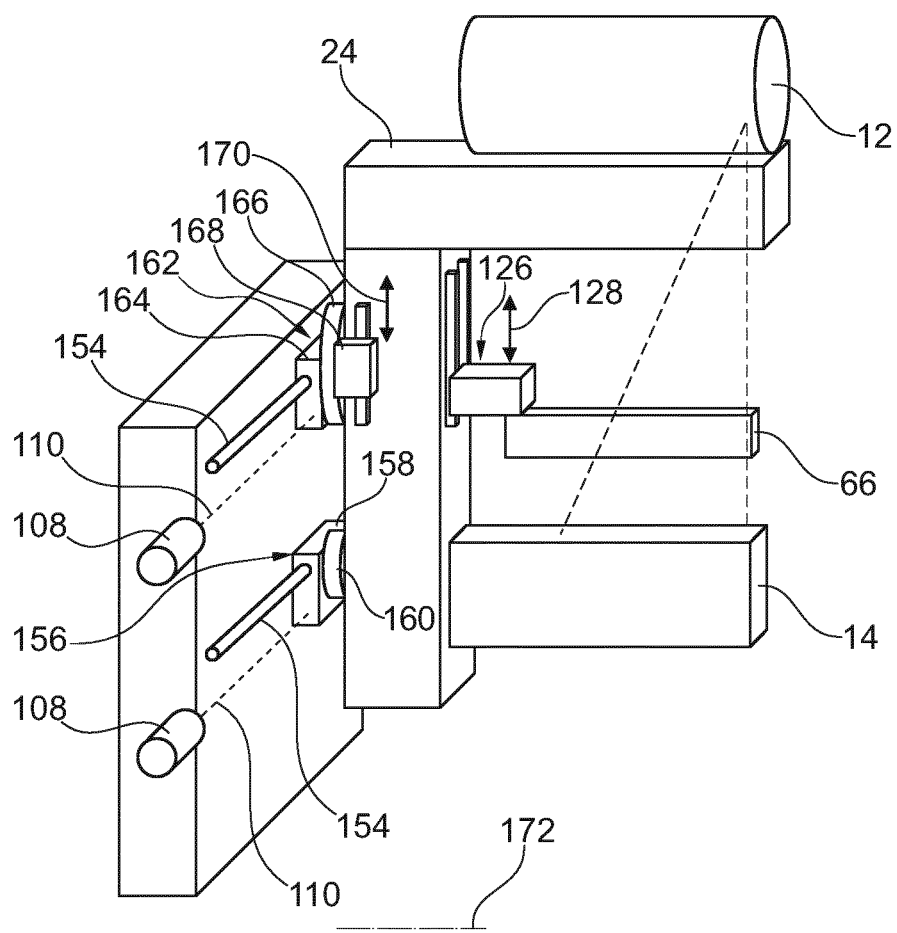
FIG. 14 shows an example of the mechanical concept with two straight guiderails.

It is noted that the above-mentioned breast support is provided, but not further shown in FIGS. 12 to 14. During the scan motion, the breast support remains fixed in relation to the imaging system 10, whereas during the scan motion, the scan arm, and, together with the scan arm, also the X-ray source, the X-ray detector, and the pre-collimator move in relation to the breast support.

The scan arm 24 is supported by the support structure 22. In order to be able to move the scan arm (to fulfil its main function), different bearings are provided, with which the scan arm is movably attached to the support structure 22.

The scan arm 24 can perform a swivelling motion around the rotation axis 26. For example, a rotational bearing 96 can be provided, as indicated in FIG. 12. The scan arm 24 is further mounted to the support structure 22 by a guiding bearing 98 that comprises a swivel joint 100 that is connected to a slide block 102 (or other type of bearing movable along a guiderail). The slide block 102 is provided for movement along a guiderail or guide 104. The guiderail 104 is shown with a straight horizontal linear extension. In another example, a curved guiderail is provided. This movement along the guide 104 is indicated with a double arrow 106. An actuator 108 is provided, which is connected, as indicated with a dotted line 110, with a further swivel joint 112 connected to the scan arm 24.

For the scan movement, the actuator 108 acts on the further swivel joint 112. Due to the support by the rotational bearing 96, the scan arm 24 is performing a swivel or pivot motion. However, to achieve that the X-ray detector 14 travels or moves along an adapted trajectory, the guiding bearing 98 holds the scan arm 24 on a respective level, Therefore, the scan arm can be provided with a telescopic connection 114 between a lower scan arm member 116 and an upper scan arm member 118. A double arrow 120 indicates the relative telescopic movement during the scan motion. The telescopic movement provides a joint with a freedom of movement in a linear direction aligned with the scan arm's vertical direction. Still further, also the further swivel joint 112 is connected to the upper scan arm member 118 with a slideable connection 122 allowing a vertical up-and-down movement 124.

As a further option, also the pre-collimator 66 is mounted to the scan arm, i.e. the upper scan arm member 118 with a slideable support 126. This slideable support 126 can be used for arranging the breast and adaptation to different heights. This slideable support 126 can also be used to move the pre-collimator 66 along an adapted trajectory during the scan motion. This is achieved by a vertical up-and-down movement 128.

In FIG. 13, an example of a mechanical concept with a lower curved guiderail 130 and two upper straight guiderails 132 is illustrated. The scan arm 24 is supported by a drive arm 134. The drive arm 134 comprises a slide block 136, or sliding bearing, that moves along the lower curved guiderail 130. The lower curved guiderail 130 is a circular arc with a centre point 138 forming a virtual rotation axis for the scan motion of the scan arm 24. The slide block 136 is connected to a drive arm member 140, which is connected to one or more further slide blocks 142 for a vertical sliding movement 144.

The actuator 108 acts on the scan arm 24 via the swivel joint 112 that is connected to the drive arm 134.

One of the two upper straight guiderails 132, e.g. the lower one of the two, is provided for guiding the scan arm 24, and with it the X-ray detector 14, in height during the scan motion. Further, also the height of the X-ray source and the pre-collimator are controlled. The slide block 102 is provided for movement along the guiderails 132.

Further, an additional bearing is provided for supporting momentum forces. This bearing is provided by the other one of the two upper straight guiderails 132, e.g. the upper one of the two. A still further slide block 146 is provided for horizontal sliding, or movement, along the upper guiderail 132. Further, the slide block 146 is connected to a further swivel joint 148 that is attached to the scan arm 24 with a further vertical slide block 150 for vertical movement 152.

In FIG. 14, an example of the mechanical concept with two straight guiderails 154 is depicted. The scan arm 24 is supported by a first bearing 156 that comprises a slide block 158 for horizontal movement along the guiderail, for example, along the lower of the two horizontal guiderails 154. A swivel joint 160 is provided for attachment to the scan arm 24. For further support, the scan arm is supported by a second bearing 162 that comprises a slide block 164 for horizontal movement along the guiderail, and a swivel joint 166 that connects the slide block 164 with a further slide block 168 for a vertical sliding movement 170 in relation to the scan arm 24. By controlling the two actuators 108 independently from each other, however in a synchronized manner, a swivelling motion of the scan arm around a virtual axis of rotation 172 can be achieved.

Figure 15:
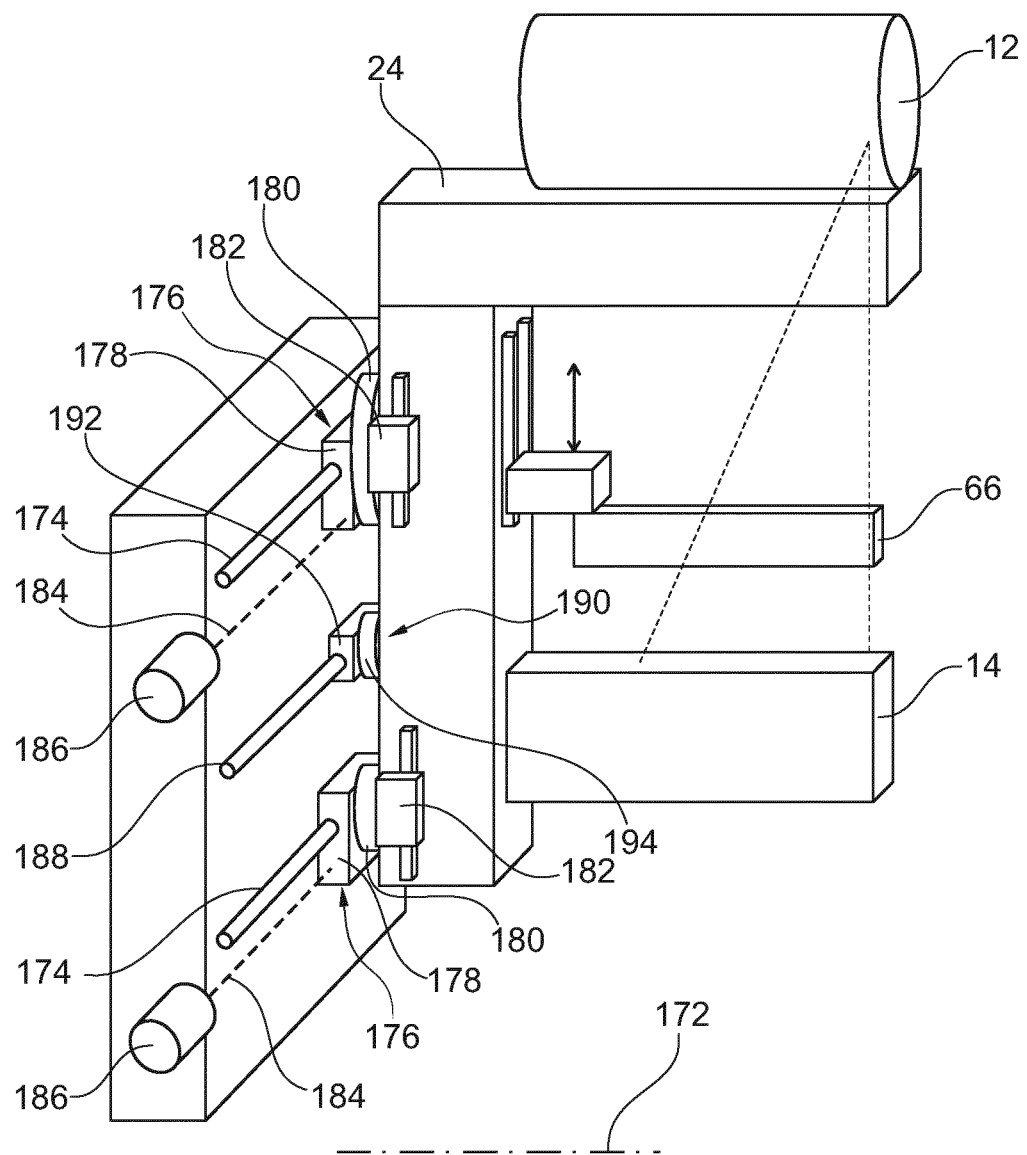
FIG. 15 shows another example of the mechanical concept with straight guiderails.

In FIG. 15, another example of the mechanical concept with straight guiderails is depicted. Two linear guiderails 174 are provided with movable bearings 176 for each guiderail to move along the respective guiderail. These two movable bearings 176 each comprise a slide block 178 for horizontal movement along the guiderail, and a swivel joint 180 that connects the slide block 178 with a further slide block 182 for a vertical sliding movement in relation to the scan arm 24. The two slide blocks 178 are further connected, as indicated with a dotted line 184, to an actuator 186.

A third guiderail 188 is provided for the carrying of the scan arm 24, and for guidance of the X-ray detector to follow the adapted trajectory.

A movable bearing 190 is provided with slide block 192 for horizontal movement along the guiderail, and a swivel joint 194 that connects the slide block 192 with the scan arm 24. The bearing 190 on the third guiderail thus provide for sliding along the guiderail as primary function, and for angular adjustment as secondary function.

The bearings 176 on the two other guiderails 174 provide for also sliding along the guiderail as primary function, and for angular adjustment as secondary function, but also for allowing vertical adjustment as third function.

The third guiderail 188 can be mounted between the upper and the lower guiderail 174, as shown in FIG. 15, but it can also be mounted above the upper guiderail or below the lower guiderail.

The two mentioned guiderails 174 are used for controlling the angle position of the scan arm, and the third guiderail 188 is used for the height control.

It is noted that the example shown in FIG. 12 also relates to the basic movement concept. The example shown in FIG. 13 also relates also to the example shown in FIGS. 8a and 8b, and the example shown in FIG. 14 also relates also to the example shown in FIGS. 9a and 9b.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A mammography X-ray imaging system for tomosynthesis mammography, comprising:
    an X-ray source;
    an X-ray detector;
    a support structure; and
    a breast support with a breast support surface;
    wherein the X-ray source and the X-ray detector are mounted on an upwardly extending scan arm; wherein the X-ray source is mounted on the scan arm above the breast support and the X-ray detector is mounted on the scan arm below the breast support;
    wherein the scan arm is movably mounted to the support structure to perform a swivelling motion about a rotation axis located below the breast support and at a position below the X-ray detector when the scan arm is in vertical position; and wherein, during the swivelling motion, the scan arm swivels about the rotation axis such that the X-ray source and the X-ray detector perform a scan motion and an object on the breast support is radiated from different angular directions;
    wherein a motion adapting mechanism is provided that, during the scan motion, moves the X-ray detector along an adapted trajectory that follows the breast support surface; and
    wherein the adapted trajectory is in alignment with the breast support surface.

2. The system according to claim 1, wherein to move the X-ray detector along the adapted trajectory that follows the breast support, the motion adapting mechanism provides a radial displacement of the X-ray detector in relation to the rotation axis during the scan motion.

3. The system according to claim 1, wherein the X-ray source and the X-ray detector are provided in a fixed relative distance to each other during operation; and wherein the motion adapting mechanism moves the X-ray source along an adapted source-trajectory that is adapted in the direction of the breast support surface.

4. The system according to claim 1, wherein the X-ray source and the X-ray detector are fixedly mounted on the scan arm; and wherein:
    the rotation axis remains fixed during a scan, and the motion adapting mechanism displaces the scan arm in relation to the rotation axis in radial direction; or
    the motion adapting mechanism provides a vertical displacement of the rotation axis, and the scan arm remains fixed in relation to the rotation axis in radial direction.

5. The system according to claim 1, wherein a pre-collimator is provided that is mounted to the scan arm; and wherein, during operation, the motion adapting mechanism moves the pre-collimator along an adapted collimator-trajectory that follows the breast support surface.

6. The system according to claim 1, wherein the motion adapting mechanism comprises at least one guiderail with an extension direction adapted to the breast support surface; and wherein the at least one guiderail provides that the X-ray detector follows the breast support surface during the scan motion.

7. The system according to claim 6, wherein the motion adapting mechanism comprises two guiderails;
    wherein one of the guiderails is provided above the breast support as an upper guiderail, and another one of the guiderails is provided below this upper guiderail as a lower guiderail;
    wherein at least one of the guiderails provides the swivelling motion of the scan arm about a virtual rotation axis, and at least another one of the guiderails provides that the X-ray detector follows the breast support surface.

8. The system according to claim 7, wherein one of the guiderails is a curved guiderail that provides the swivelling motion of the scan arm about a virtual rotation axis, and the other one of the guiderails is an at least less-curved guiderail that provides that the X-ray detector follows the breast support surface.

9. The system according to claim 8, wherein it is provided that:
    the upper guiderail is the curved guiderail, and the lower guiderail is the less-curved guiderail; wherein two movable bearings for the scan arm are provided to move along the upper, curved guiderail for swivelling the scan arm during the scan motion, and the two movable bearings are having a fixed distance to each other in direction of the guiderail; and wherein the lower guiderail provides for the carrying of the scan arm and for guidance of the X-ray detector to follow the adapted trajectory; or
    the upper guiderail is the less-curved guiderail, and the lower guiderail is the curved guiderail; wherein two movable bearings for the scan arm are provided to move along the lower, curved guiderail for swivelling the scan arm during the scan motion, and the two movable bearings are having a fixed distance to each other in direction of the guiderail; and wherein the upper guiderail provides for the carrying of the scan arm, and for guidance of the X-ray detector to follow the adapted trajectory.

10. The system according to claim 9, wherein a third guiderail is provided;
    wherein the third guiderail is less-curved than the lower, curved guiderail; and wherein the third guiderail provides for support of carrying of the scan arm, and for guidance of the X-ray detector to follow the adapted trajectory; and
    wherein the upper guiderail provides for additional support of the scan arm.

11. The system according to claim 7, wherein at least two guiderails are provided as linear guiderails;
    wherein movable bearings are provided for each guiderail to move along the respective guiderail;

wherein the swivel motion of the scan arm is provided by a synchronized movement of at least two movable bearings along two of the at least two guiderails; and wherein one of the at least two guiderails provides that the X-ray detector follows the breast support surface.

12. The system according to claim 1, wherein the surface of the breast support is provided as a concave surface for supporting a breast; and wherein during the scan motion, the X-ray detector moves along an arc trajectory, which arc is having a virtual rotation axis arranged above the breast support.

13. The system according to claim 1, wherein the X-ray detector is a line-detector comprising a plurality of strip detector segments; and/or the X-ray detector is a photon-counting detector.

14. A method for providing mammography X-ray image data for tomosynthesis mammography, the method comprising:

arranging an object of interest on a breast support surface of a breast support; and scanning the object with radiation provided from an X-ray source towards an X-ray detector; wherein the X-ray source and the X-ray detector are mounted on an upwardly extending scan arm; wherein the X-ray source is mounted on the scan arm above the breast support and the X-ray detector is mounted on the scan arm below the breast support; and wherein the scan arm is movably mounted to a support structure to perform a swivelling motion about a rotation axis located below the breast support and at a position below the X-ray detector when the scan arm is in vertical position;

wherein, during the scanning, the scan arm is swivelling about the rotation axis such that the X-ray source and the X-ray detector perform a scan motion and the object on the breast support is radiated from different angular directions; and wherein, during the scanning, a motion adapting mechanism is moving the X-ray detector along an adapted trajectory that follows the breast support surface; and wherein, during the scanning, X-ray radiation that has passed the object is detected by the detector.

* * * * *